United States Patent
Kawabata et al.

(10) Patent No.: US 11,832,993 B2
(45) Date of Patent: Dec. 5, 2023

(54) ULTRASOUND DIAGNOSTIC DEVICE AND ULTRASOUND SIGNAL PROCESSING METHOD

(71) Applicant: Konica Minolta, Inc., Tokyo (JP)

(72) Inventors: Akihiro Kawabata, Hachioji (JP); Yoshihiro Takeda, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 34 days.

(21) Appl. No.: 17/366,872

(22) Filed: Jul. 2, 2021

(65) Prior Publication Data

US 2022/0008042 A1 Jan. 13, 2022

(30) Foreign Application Priority Data

Jul. 9, 2020 (JP) .................................. 2020-118463

(51) Int. Cl.
*A61B 8/08* (2006.01)
*A61B 8/00* (2006.01)

(52) U.S. Cl.
CPC .......... *A61B 8/5246* (2013.01); *A61B 8/4494* (2013.01); *A61B 8/5207* (2013.01)

(58) Field of Classification Search
CPC ... A61B 8/5246; A61B 8/4494; A61B 8/5207; A61B 8/488; A61B 8/54; G01S 15/8995; G01S 7/52085; G01S 15/8979
See application file for complete search history.

(56) References Cited

U.S. PATENT DOCUMENTS 3,888,238 A * 6/1975 Meindl .................... A61B 8/06
367/90
6,537,217 B1 3/2003 Bjærum et al.
(Continued)

FOREIGN PATENT DOCUMENTS

CN 108261208 A * 7/2018 ............. A61B 8/486
JP H04-317639 A 11/1992
(Continued)

*Primary Examiner* — Shahdeep Mohammed
*Assistant Examiner* — Fikirte (Fiki) T Ashine
(74) *Attorney, Agent, or Firm* — LUCAS & MERCANTI, LLP

(57) ABSTRACT

An ultrasound diagnostic device including a transmitter, a first image processor, a second image processor, and an image synthesizer. The transmitter alternates between first transmission events that include transmission of first detection waves and second transmission events that include transmission of second detection waves. The first image processor generates frames of first images based on reception signals corresponding to a plurality of the first transmission events. The second image processor generates frames of second images based on reception signals corresponding to the second transmission events. The image synthesizer superimposes the second images on the first images to generate synthesized images. Frame rate of the second images is higher than that of the first images. The transmitter performs a third transmission event prior to the second transmission events that includes transmission of a plurality of the first detection waves to acquire reception signals corresponding to one frame of the first images.

22 Claims, 12 Drawing Sheets

(56) References Cited

U.S. PATENT DOCUMENTS

| | | | |
|---|---|---|---|
| 2003/0045795 A1* | 3/2003 | Bjaerum | G01S 7/52034 600/441 |
| 2005/0283078 A1* | 12/2005 | Steen | A61B 8/463 600/447 |
| 2009/0124905 A1* | 5/2009 | Ahn | G01S 7/52085 600/443 |
| 2012/0101384 A1* | 4/2012 | Migita | A61B 8/06 600/443 |
| 2014/0180106 A1* | 6/2014 | Takahashi | A61B 8/467 600/443 |
| 2018/0092627 A1* | 4/2018 | Susumu | A61B 8/4494 |
| 2018/0206820 A1* | 7/2018 | Anand | G01S 7/52085 |

FOREIGN PATENT DOCUMENTS

| | | |
|---|---|---|
| JP | H09-245990 A | 9/1997 |
| JP | 2001-218759 A | 8/2001 |
| JP | 2003-111759 A | 4/2003 |
| JP | 2011-526181 A | 10/2011 |
| JP | 2017-080493 A | 5/2017 |
| JP | 2018-102771 A | 7/2018 |
| JP | 2018-134448 A | 8/2018 |

\* cited by examiner

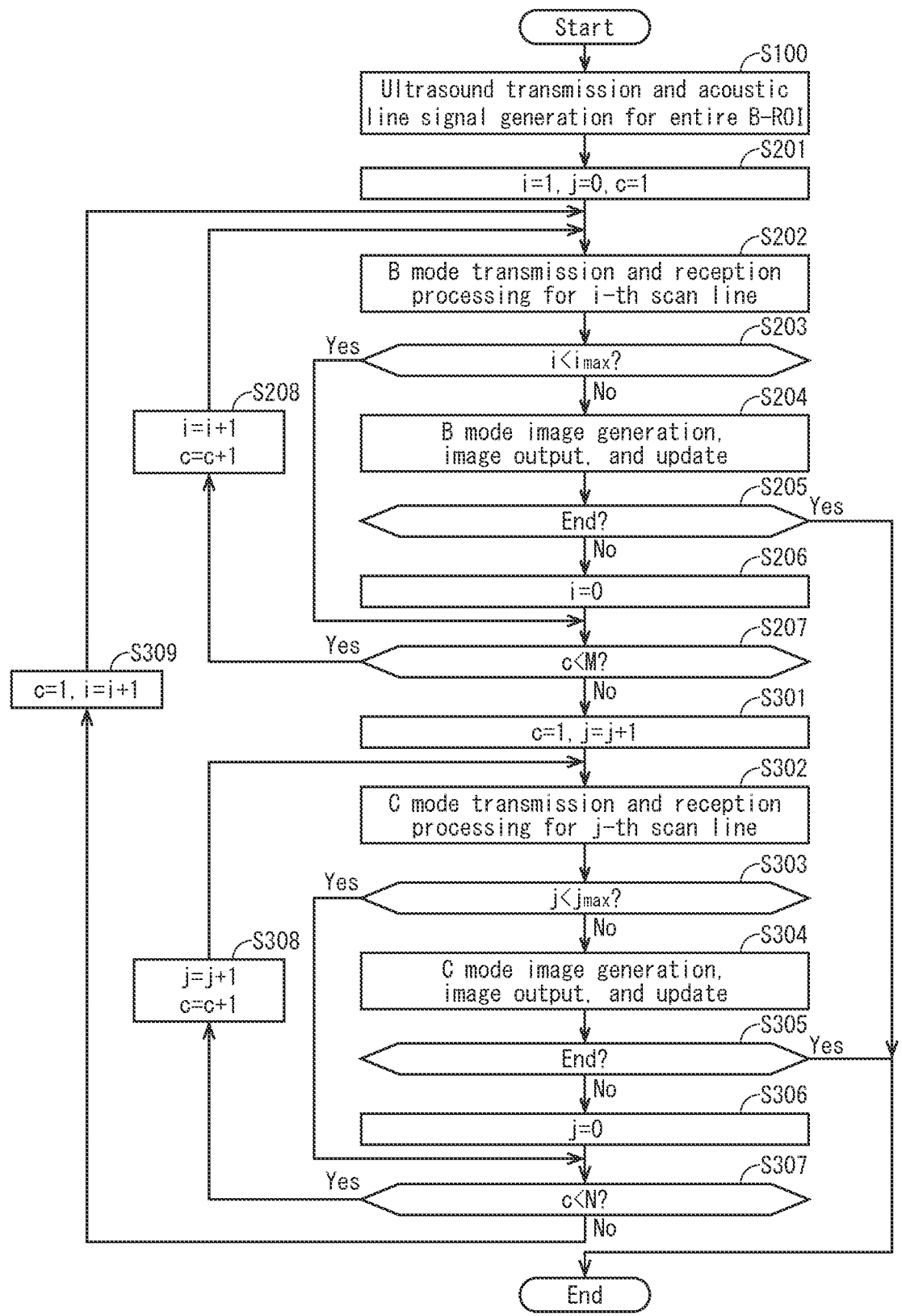

ULTRASOUND DIAGNOSTIC DEVICE AND ULTRASOUND SIGNAL PROCESSING METHOD

This application claims priority to Japanese Patent Application No. 2020-118463, filed Jul. 9, 2020, the contents of which are hereby incorporated by reference in their entirety.

BACKGROUND

Technical Field

The present disclosure relates to ultrasound diagnostic devices and ultrasound transmission and reception methods used in color flow mapping.

Background Art

In ultrasound diagnosis, a heartbeat and fetal movement can be measured in real time by simply applying an ultrasound probe to a body surface, and this measurement is very safe so repeated examinations can be performed.

An ultrasound diagnostic device images internal information of a subject as ultrasound images based on reflected ultrasound obtained by transmitting and receiving ultrasound into the subject via an ultrasound probe. Such ultrasound images may include B mode images obtained in a brightness (B) mode and C mode images obtained in a color flow (C) mode (color Doppler images). A B mode image is an image of internal tissue of a subject displaying amplitude intensity of reflected ultrasound in terms of brightness. On the other hand, a C mode image is an image in which blood flow information is displayed in color in a region of interest (ROI) specified in a B mode image. More specifically, blood flow information in an ROI is typically superimposed on B mode images with blood flow approaching the ultrasound probe in red and blood flow away from the ultrasound probe in blue.

In order to superimpose a C mode image on a B mode image, both a B mode image scan and a C mode image scan are required, and therefore there is a technical problem of a decrease in frame rate. Accordingly, as disclosed in JP 2003-111759, a technique has been proposed in which a frame rate of C mode images is higher than a frame rate of B mode images. Further, for example, as disclosed in JP 2017-080493 and JP 2018-102771, a technique has been proposed in which a portion of B mode image scanning is performed in breaks between frames of C mode image scanning. According to these techniques, C mode image frame rate can be improved and tracking speed of blood flow visualization can be increased.

SUMMARY

According to the techniques of JP 2003-111759, JP 2017-080493, and JP 2018-102771, the frame rate of B mode images is lower than the frame rate of C mode images, and therefore there is a technical problem that drawing of a first frame of B mode images is intermittent with respect to drawing of C mode images. Further, and this is not limited to B mode images and C mode images, when scanning for two different image modes is alternated, there is also a technical problem that first frame drawing of the image mode with a low frame rate is delayed compared to drawing of the image mode with a high frame rate.

The present disclosure is made in view of the technical problems above, and an object of the present disclosure is to provide a configuration that promptly starts drawing in two image modes having different frame rates.

To achieve at least the abovementioned object, according to an aspect of the present disclosure, an ultrasound diagnostic device reflecting an aspect of the present disclosure is an ultrasound diagnostic device that generates images by transmitting and receiving ultrasound to and from a subject via a probe, the ultrasound diagnostic device comprising: ultrasound signal processing circuitry, the ultrasound signal processing circuitry comprising: a transmitter, a receiver, a first image processor, a second image processor, and an image synthesizer. The transmitter alternates between first transmission events that each include transmission of first detection waves and second transmission events that each include transmission of second detection waves. The receiver receives signals based on reflected ultrasound and generates reception signals from the signals. The first image processor repeatedly performs an operation of generating a frame of first images based on reception signals corresponding to a plurality of the first transmission events. The second image processor repeatedly performs an operation of generating a frame of second images based on reception signals corresponding to the second transmission events. The image synthesizer superimposes the second images on the first images to generate and output synthesized images. Frame rate of the second images is higher than frame rate of the first images. The transmitter performs a third transmission event prior to the second transmission events, the third transmission event including transmission of a plurality of the first detection waves to acquire reception signals corresponding to one frame of the first images. The first image processor generates one frame of the first images based on the reception signals corresponding to the third transmission event.

BRIEF DESCRIPTION OF DRAWINGS

These and other objects, advantages, and features of the technology pertaining to the present disclosure will become apparent from the following description thereof taken in conjunction with the accompanying drawings, which illustrate at least one embodiment of the technology pertaining to the present disclosure.

FIG. 6 is a flowchart illustrating operations of an ultrasound diagnostic device 100 pertaining to Embodiment 1.

DETAILED DESCRIPTION

Embodiment 1

Overall Structure

The following is a description of an ultrasound diagnostic device 100 pertaining to an embodiment, described with reference to the drawings.

Figure 1:
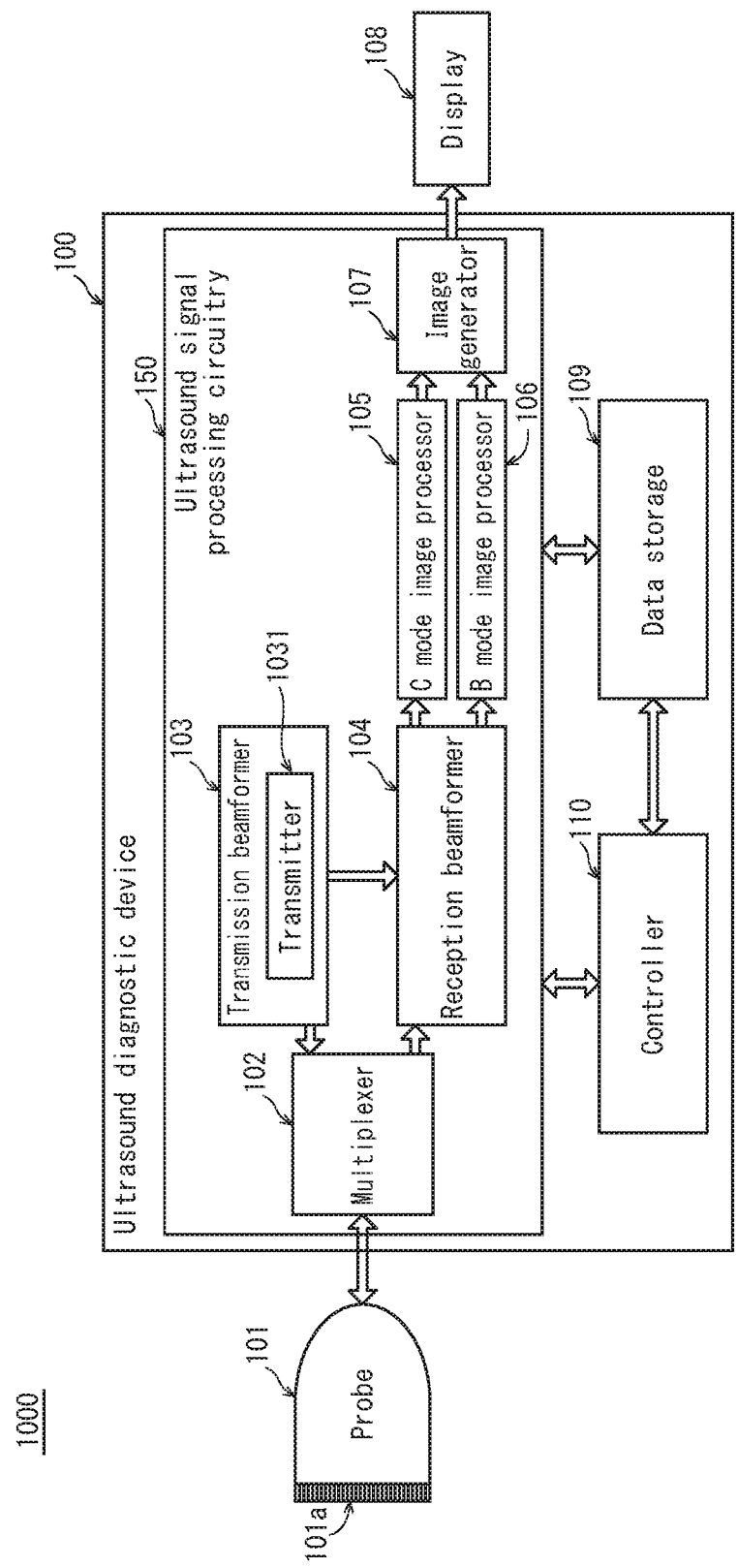
FIG. 1 is a function block diagram of an ultrasound diagnostic system 1000 pertaining to Embodiment 1.

FIG. 1 is a function block diagram of an ultrasound diagnostic system 1000 pertaining to at least one embodiment. As illustrated in FIG. 1, the ultrasound diagnostic system 1000 includes: a probe 101 that includes transducers 101a that transmit ultrasound towards a subject and receive resultant reflected waves; the ultrasound diagnostic device 100 that causes the probe 101 to transmit and receive ultrasound and generates ultrasound images based on output signals from the probe 101; and a display 108 that displays the ultrasound images on a screen. The probe 101 and the display 108 are each connectable to the ultrasound diagnostic device 100. In FIG. 1, the probe 101 and the display 108 are illustrated connected to the ultrasound diagnostic device 100. The probe 101 and the display 108 may be integrated with the ultrasound diagnostic device 100.

Structure of Ultrasound Diagnostic Device 100

The ultrasound diagnostic device 100 includes: a multiplexer 102 that selects transducers to be used for each transmission or reception from among the transducers 101a of the probe 101 and secures input/output to the selected transducers; a transmission beamformer 103 that controls timing of high voltage application to the transducers 101a of the probe 101 for ultrasound transmission; and a reception beamformer 104 that amplifies electric signal obtained by the transducers 101a based on reflected ultrasound received by the probe 101, performs analogue/digital (A/D) conversion, and generates acoustic line signals by reception beamforming. The ultrasound diagnostic device 100 further includes: a C mode image processor 105 that frequency-analyzes output signals from the reception beamformer 104 and generates color flow information; a B mode image processor 106 that generates frame B signals corresponding to B mode images (tomographic images) based on output signals from the reception beamformer 104; an image generator 107 that converts frame B signals to B mode images, superimposes color flow information to generate color Doppler images, and causes the color Doppler images to be displayed on the display 108; a data storage 109 that stores acoustic line signals output by the reception beamformer 104, frame cubic frequency modulated (CFM) signals output by the C mode image processor 105, and frame B signals output by the B mode image processor 106; and a controller 110 that controls each component.

Of these, the multiplexer 102, the transmission beamformer 103, the reception beamformer 104, the C mode image processor 105, the B mode image processor 106, and the image generator 107 constitute ultrasound signal processing circuitry 150.

Elements of the ultrasound diagnostic device 100, for example the multiplexer 102, the transmission beamformer 103, the reception beamformer 104, the C mode image processor 105, the B mode image processor 106, the image generator 107, and the controller 110, are each realized by hardware circuitry such as field programmable gate arrays (FPGA), application specific integrated circuits (ASIC), or the like.

The data storage 109 is a computer-readable storage medium, and may be a flexible disk, a hard disk, magneto-optical (MO), optical media, semiconductor memory, or the like. Further, the date storage 109 may be a storage device that is external and connectable to the ultrasound diagnostic device 100.

The ultrasound diagnostic device 100 pertaining to Embodiment 1 is not limited to the structure illustrated in FIG. 1. For example, a structure is possible without the multiplexer 102, where the transmission beamformer 103 and the reception beamformer 104 are directly connected to the transducers 101a of the probe 101. Further the probe 101 may incorporate the transmission beamformer 103, the reception beamformer 104, or a portion of either or both of the transmission beamformer 103 and the reception beamformer 104. This does not only apply to the ultrasound diagnostic device 100 pertaining to Embodiment 1, the same applies to the ultrasound diagnostic devices pertaining to other embodiments and modifications described in this disclosure.

Description of Components

1. Transmission Beamformer 103

The transmission beamformer 103 is connected to the probe 101 via the multiplexer 102 and controls timing of high voltage application to each transducer included in a transmission aperture Tx composed of a transmission transducer array consisting of all or some of the transducers 101a of the probe 101, for the purpose of transmitting ultrasound from the probe 101. The transmission beamformer 103 includes a transmitter 1031.

Based on a transmission control signal from the controller 110, the transmitter 1031 performs transmission processing to supply a pulse-shaped transmission signal for causing transmitters included in the transmission aperture Tx among the transmitters 101a of the probe 101 to transmit an ultrasound beam. The transmitter 1031 includes, for example, clock generation circuitry, pulse generation circuitry, and delay circuitry. The clock generation circuitry is circuitry that cause generation of a clock signal that determines ultrasound beam transmission timing. The pulse generation circuitry is circuitry for causing generation of a pulse signal that drives transducers. The delay circuitry is circuitry that sets a delay time for ultrasound beam transmission timing for each transducer, for focusing ultrasound beams by delaying ultrasound beam transmission by the delay time.

Figure 2A:
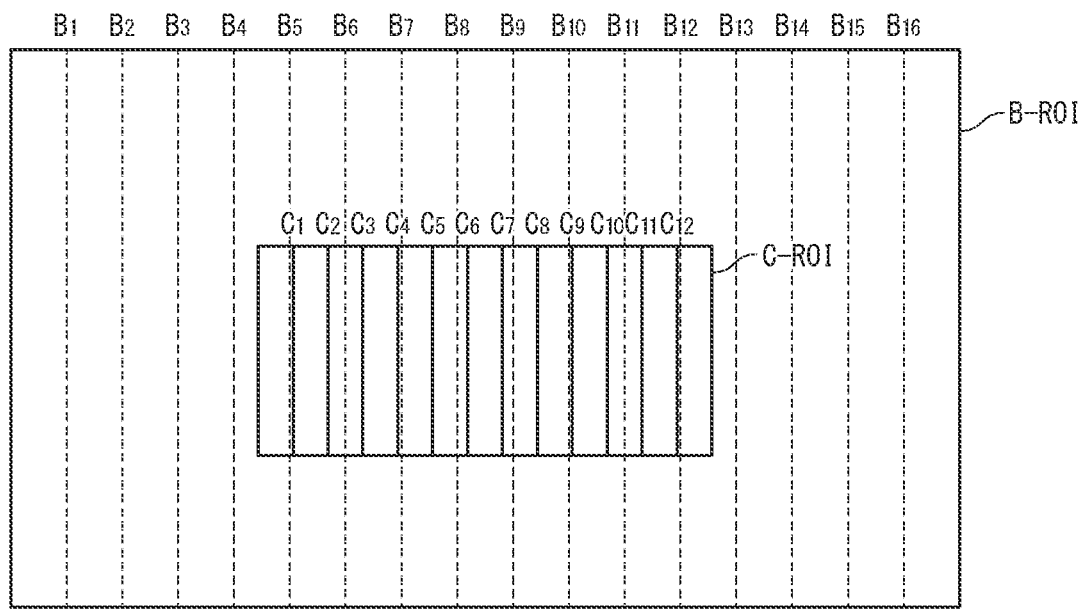
FIG. 2A is a schematic diagram illustrating target regions for ultrasound transmission and reception in B mode transmission and C mode transmission.

The transmitter 1031 divides time between ultrasound transmission for generating B mode images (hereinafter also referred to as "B mode transmission") and ultrasound transmission for generating C mode images (hereinafter also referred to as "C mode transmission") (this process hereinafter also referred to as "time division"). FIG. 2A is a schematic diagram illustrating target regions for ultrasound transmission and reception in B mode transmission and C mode transmission. In FIG. 2A, "B-ROI" indicates a region of interest (ROI) as a target region for B mode images and "C-ROI" indicates an ROI as a target region for C mode images. Here, the C-ROI is included in the B-ROI, but a relationship between B-ROI and C-ROI is not limited to this example. The ultrasound diagnostic device 100 sets scan lines B1 to B16 for the B-ROI, and performs ultrasound transmission and reception on each of the scan lines. Similarly, the ultrasound diagnostic device 100 sets scan lines C1 to C12 for the C-ROI, and performs ultrasound transmission and reception on each of the scan lines. The scan lines in the B-ROI and the scan lines in the C-ROI are just examples, and the number, direction, and intervals between may be set arbitrarily.

In B mode transmission, the transmitter 1031 causes transmission of a detection wave focusing (converging) at a transmission focal point F provided at a defined depth (focal depth) on or near a scan line. More specifically, transmission timing of each transducer is controlled so that the closer a transducer is to the transmission focal point F, the more transmission timing is delayed. The position of a focal point F is determined relative to scan line position and focal depth. Similarly, in C mode transmission, the transmitter 1031 causes transmission of a detection wave focusing (converging) at a transmission focal point F provided at a defined depth (focal depth) on or near a scan line. Focal depth in B mode transmission and focal depth in C mode transmission may be the same, and may be depth of a center position of the B-ROI and depth of a center position of the C-ROI, respectively. Relative positions between transmission focal points F and scan lines are not limited to the examples above, and may be set arbitrarily.

Figure 3:
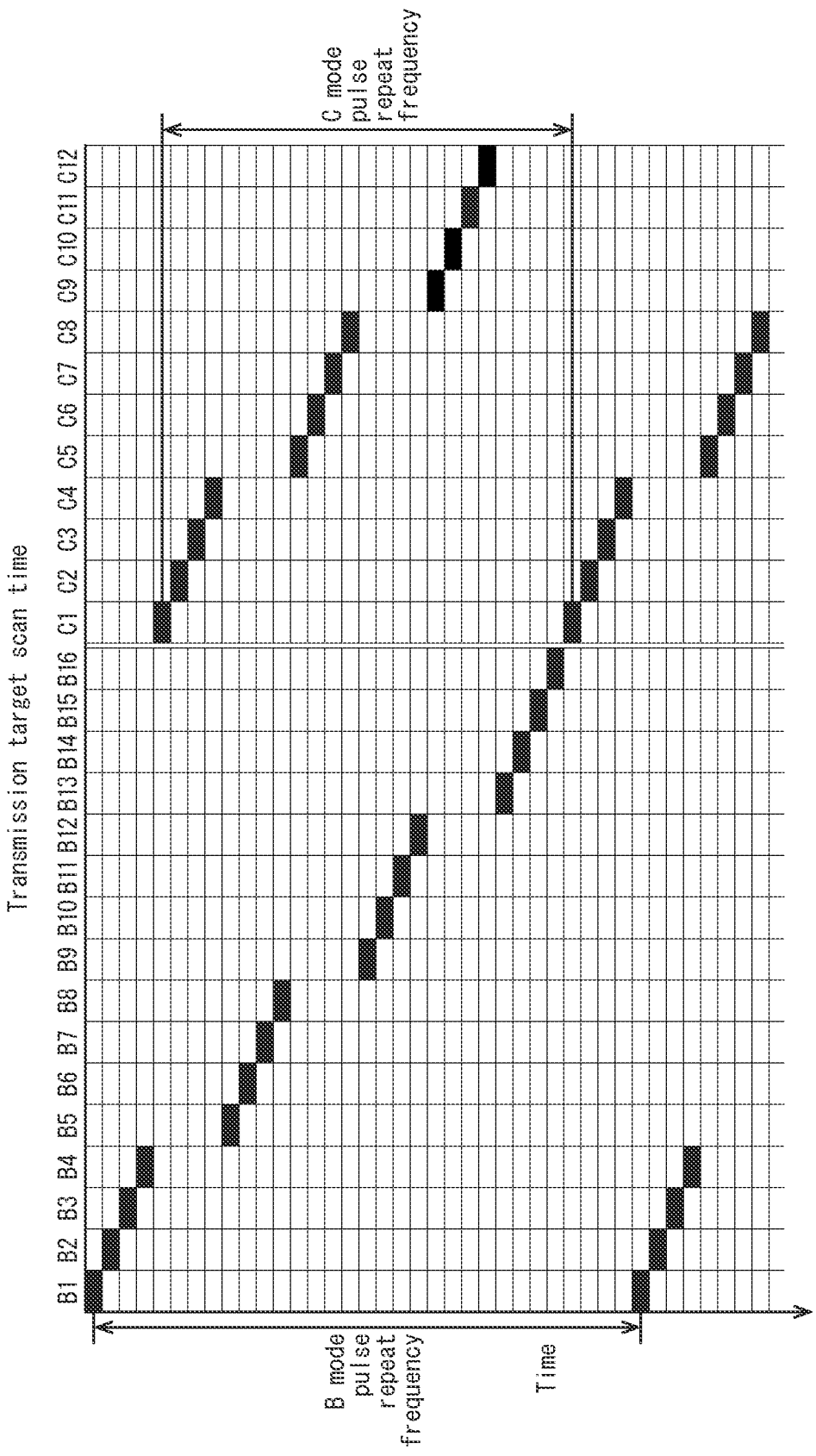
FIG. 3 is a time chart illustrating a relationship between transmission order and scan line position pertaining to Embodiment 1.

The following describes in detail the ordering of B mode transmission and C mode transmission. The transmitter alternately causes performance of M consecutive B mode transmissions (M is a natural number) and N consecutive C mode transmissions (N is a natural number). Hereinafter, M consecutive B mode transmissions are referred to as a B mode transmission event, N consecutive C mode transmissions are referred to as a C mode transmission event, and when B mode and C mode are not distinguished, they are referred to as transmission events. FIG. 3 is a time chart illustrating a relationship between transmission order and scan line position. In FIG. 3, the horizontal axis indicates scan line position, and the vertical axis indicates time. The transmitter 1031 causes B mode transmission four times, in the order of scan lines B1, B2, B3, B4. In other words, in the present example, M=4. Next, C mode transmission is performed four times, in the order of scan lines C1, C2, C3, C4. In other words, in the present example, N=4. Specific values of M and N are not limited to these examples, and M and N may be different. Next, B mode transmission is performed four times, in the order of scan lines B5, B6, B7, B8. Next, C mode transmission is performed four times, in the order of scan lines C5, C6, C7, C8. Next, B mode transmission is performed four times, in the order of scan lines B9, B10, B11 B12. Next, C mode transmission is performed four times, in the order of scan lines C9, C10, C11, C12. As a result, C mode transmission has completed one cycle, that is, transmission of one frame is completed. Next, B mode transmission is performed four times, in the order of scan lines B13, B14, B15 B16. As a result, B mode transmission has completed one cycle, that is, transmission of one frame is completed. Next, C mode transmission is performed four times from the beginning, that is, in the order of scan lines C1, C2, C3, C4. According to this example, for B mode transmission, the time for 32 transmissions is a pulse repetition frequency, and for C mode transmission, the time for 24 transmissions is a pulse repetition frequency.

Figure 4:
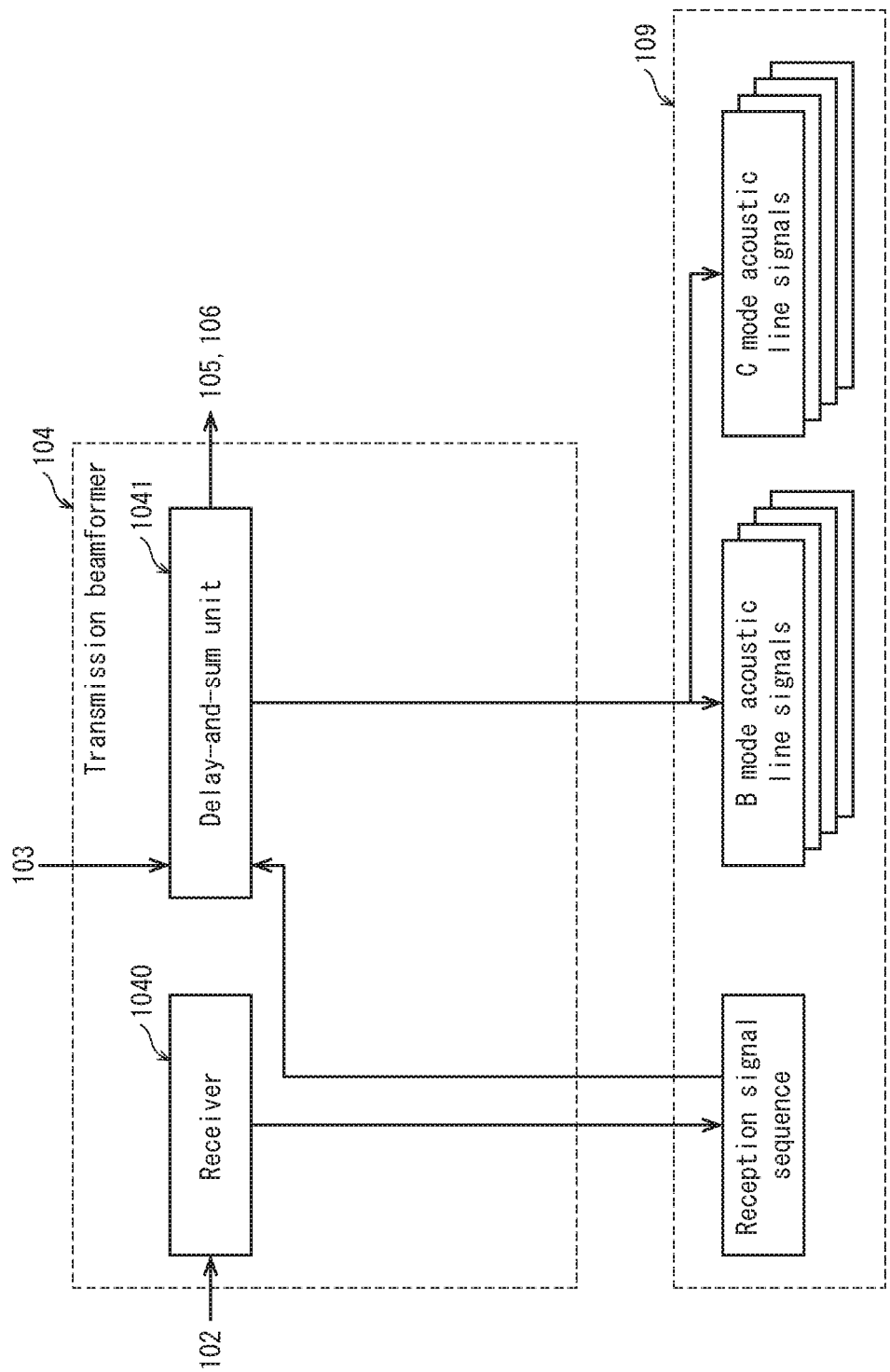
FIG. 4 is a function block diagram of a reception beamformer 104 pertaining to Embodiment 1.

The reception beamformer 104 generates acoustic line signals from electrical signals obtained by the transducers 101a, based on reflections of ultrasound received by the probe 101. Here, "acoustic line signals" are signals after delay-and-sum processing with respect to observation points. Delay-and-sum processing is described in more detail later. FIG. 4 is a function block diagram of the reception beamformer 104. As illustrated in FIG. 4, the reception beamformer 104 includes a receiver 1040 and a delay-and-sum unit 1041.

The following describes components that constitute the reception beamformer 104.

(1) Receiver 1040

The receiver 1040 is connected to the probe 101 via the multiplexer 102, and is circuitry that amplifies and converts from analogue to digital the electrical signals obtained by the probe 101 from received reflected ultrasound, to generate reception signals (radio frequency (RF) signals) synchronized with B mode transmission or C mode transmission. The reception signals generated in synchronization with B mode transmission or C mode transmission are output to the data storage 109 and stored in the data storage 109.

Here, a reception signal (RF signal) is a digital signal obtained by analogue-to-digital conversion of an electrical signal converted from reflected ultrasound received by a transducer, and is composed of a series of signals that are continuous in a transmission direction (depth direction of subject) of ultrasound received by the transducer.

In B mode transmission and C mode transmission, as described above, the transmitter 1031 causes transmission of an ultrasound beam from the probe 101 so that ultrasound is focused on or near a scan line set in the subject. Based on reflected ultrasound obtained by some or all transducers among the transducers 101a of the probe 101 in synchronization with B mode transmission or C mode transmission, the receiver 1040 generates a reception signal sequence for each transducer. Here, a transducer that receives reflected ultrasound is also referred to as a "reception transducer".

The receiver 1040 generates a reception signal series for each reception transducer, synchronized with the B mode transmission or the C mode transmission, and generated reception signals are stored in the data storage 109.

(2) Delay-and-Sum Unit 1041

The delay-and-sum unit 1041 generates acoustic line signals with respect to the subject in synchronization with B mode transmission or C mode transmission. Specifically, observation points are provided on scan line Bx (x=1 to 16) or scan line Cy (y=1 to 12). Then, for each observation point, reception signals arriving at each reception transducer from the observation point are identified and summed (delay-and-sum). In this way, for each observation point, an acoustic line signal that is a reception signal is generated.

The delay-and-sum unit 1041 generates acoustic line signals corresponding to scan lines, synchronized with the B mode transmission or the C mode transmission, and generated acoustic line signals are stored in the data storage 109. Acoustic line signals include B mode acoustic line signals based on reception signals obtained corresponding to B mode transmission and C mode acoustic line signals based on reception signals obtained corresponding to C mode transmission.

3. C Mode Image Processor 105

Figure 5:
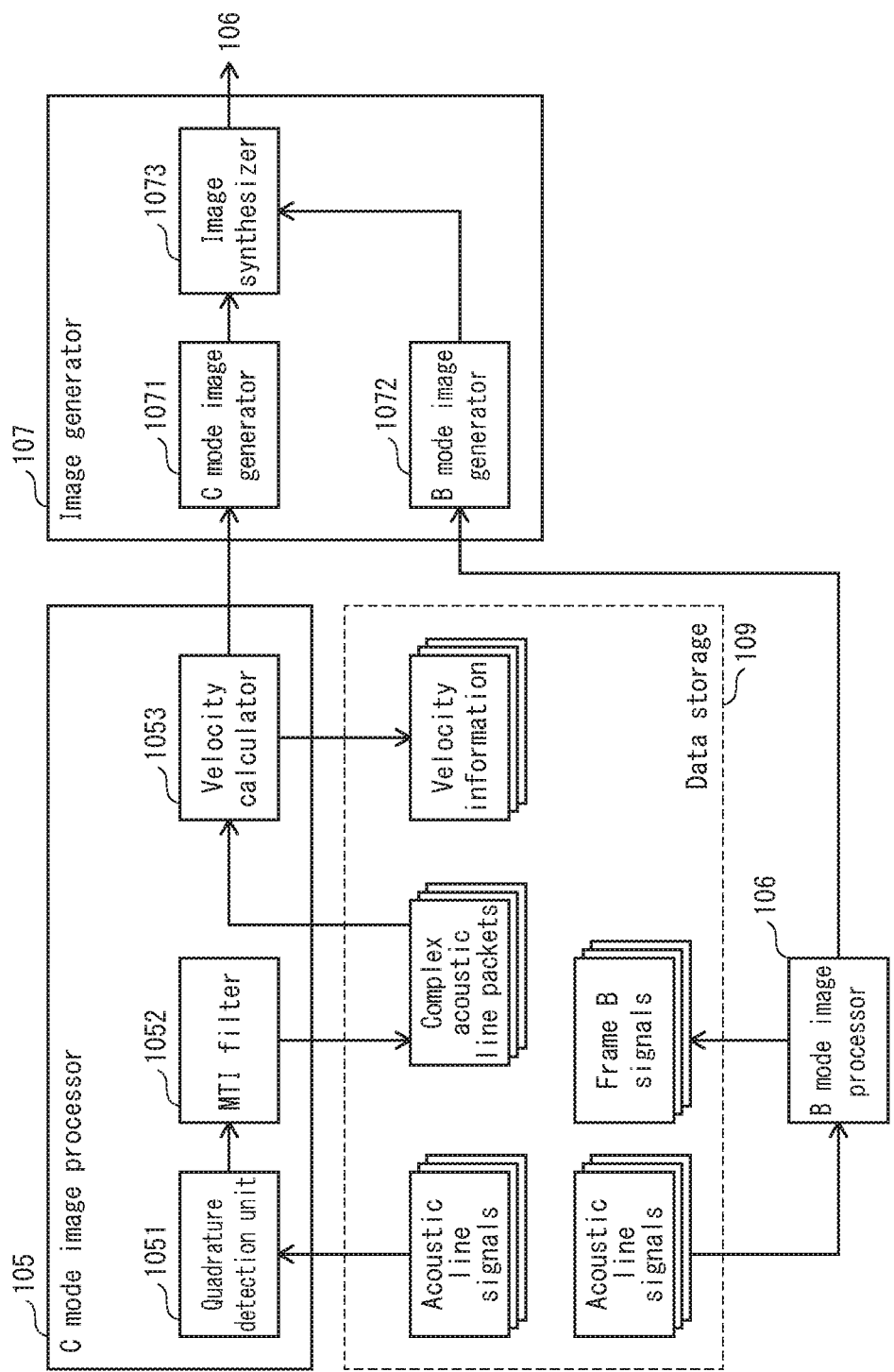
FIG. 5 is a function block diagram illustrating a C mode image processor 105, a B mode image processor 106, and an image generator 107 pertaining to Embodiment 1.

The C mode image processor 105 performs frequency analysis to generate CFM signals based on C mode acoustic line signals obtained corresponding to C mode transmissions. Here, a "CFM signal" is a signal indicating velocity information for an observation point. Velocity information is described in more detail later. FIG. 5 is a function block diagram illustrating the C mode image processor 105, the B mode image processor 106, and the image generator 107. As illustrated in FIG. 5, the C mode image processor 105 includes a quadrature detection unit 1051, a filter unit 1052, and a velocity calculator 1053.

The following describes components that constitute the C mode image processor 105.

(1) Quadrature Detection Unit 1051

The quadrature detection unit 1051 is circuitry that performs quadrature detection for each C mode acoustic line signal and generates complex acoustic line signals indicating phase of reception signals at each observation point. More specifically, the following processing is performed. First a first reference signal having a reference frequency and a second reference signal having a phase 90° different from that of the first reference signal are generated. The reference frequency is, for example, the same frequency as the detection wave. Next, the acoustic line signal and the first reference signal are integrated, and a high frequency component having a frequency about twice that of the reference frequency is removed by a low pass filter (LPF) to obtain a first component. Next, the acoustic line signal and the second reference signal are integrated, and a high frequency component having a frequency about twice that of the reference frequency is removed by an LPF to obtain a second component. Finally, a complex acoustic line signal is generated with the first component as the real part (I component; in-phase) and the second components as the imaginary part (Q component: quadrature phase).

(2) Filter Unit 1052

The filter unit 1052 is filter circuitry that removes clutter from the complex acoustic line signals. Here, clutter means components of tissue movement that is not a target for imaging, specifically information indicating movement of tissue such as blood vessel walls, muscles, and organs. Clutter has more power than a signal indicating blood flow, but tissue movement is slower than that of blood flow and therefore clutter has a lower frequency than a signal indicating blood flow. Accordingly, it is possible to selectively remove only clutter from the signals. The filter unit 1052 can apply known techniques such as a "wall filter" or "moving target indicator (MTI) filter".

The filter unit 1052 stores the complex acoustic line signals after filtering as complex acoustic line packets in the data storage 109.

(3) Velocity Calculator 1053

The velocity calculator 1053 is circuitry that estimates movement in a subject, specifically blood flow, corresponding to each observation point from the complex acoustic line signals after filtering. The velocity calculator 1053, for each observation point, estimates phase from each complex acoustic line signal corresponding to C mode transmissions, and calculates phase change rate. Specifically, a complex acoustic line signal corresponding to multiple C mode transmissions is read out as a complex acoustic line packet for each observation point, and a phase change rate of the complex acoustic line signal is estimated. As a method of estimating phase change rate, a phase of each complex acoustic line signal may be specified to calculate an amount of phase change per unit of time, or correlation processing between complex acoustic line signals may be performed to calculate an amount of phase change per unit of time. The velocity calculator stores velocity calculated for each observation point as velocity information in the data storage 109.

4. B Mode Image Processor 106

The B mode image processor 106 performs envelope detection and logarithmic compression on values of acoustic line signals obtained corresponding to B mode transmission to generate frame B signals, then synthesizes B signals to generate frame B signals, which are each one frame worth of synthesized B signals. The B mode image processor 106 outputs frame B signals to the image generator 107 and the data storage 109.

5. Image Generator 107

The image generator 107 is circuitry for converting frame B signals generated by the B mode image processor 106 into B mode images, and color-converting velocity information generated by the C mode image processor 105 to superimpose onto B mode images to generate color Doppler images. As illustrated in FIG. 5, the image generator 107 includes a C mode image generator 1071, a B mode image generator 1072, and an image synthesizer 1073.

(1) C Mode Image Generator 1071

The C mode image generator 1071 is circuitry that performs color mapping for generating color Doppler images from velocity information. Specifically, first, a coordinate system of velocity information is converted into a Cartesian coordinate system. Next, velocity at each observation point is converted into color information to generate color flow information. At this time, for example, conversion is performed such that (1) towards the probe is red, away from the probe is blue, and (2) the larger an absolute value of velocity, the higher the saturation, and the smaller the absolute value, the lower the saturation. More specifically, an absolute value of velocity is converted into a red luminance value for velocity components towards the probe, and an absolute value of velocity is converted into a blue luminance value for velocity components away from the probe.

The C mode image generator 1071 may further receive a signal indicating velocity dispersion from the C mode image processor 105, and convert dispersion values into green luminance values. By doing so, positions where turbulence occurs can be indicated.

The C mode image generator 1071 outputs generated color Doppler images to the image synthesizer 1073.

(2) B Mode Image Generator 1072

The B mode image generator 1072 is circuitry that generates B mode images from frame B signals. Specifically, first, a coordinate system of frame B signals is converted to a Cartesian coordinate system. Next, value of B signals for each observation point are converted into luminance values to generate B mode images. The B mode image generator 1072 outputs generated B mode images to the image synthesizer 1073.

(3) Image Synthesizer 1073

The image synthesizer 1073 is circuitry that superimposes C mode images generated by the C mode image generator 1071 onto B mode images generated by the B mode image generator 1072 to generate color Doppler images, and outputs to the display 108. As a result, a color Doppler image in which direction and speed (absolute value of velocity) of blood flow is added to a B mode image is displayed on the display 108.

Figure 2B:
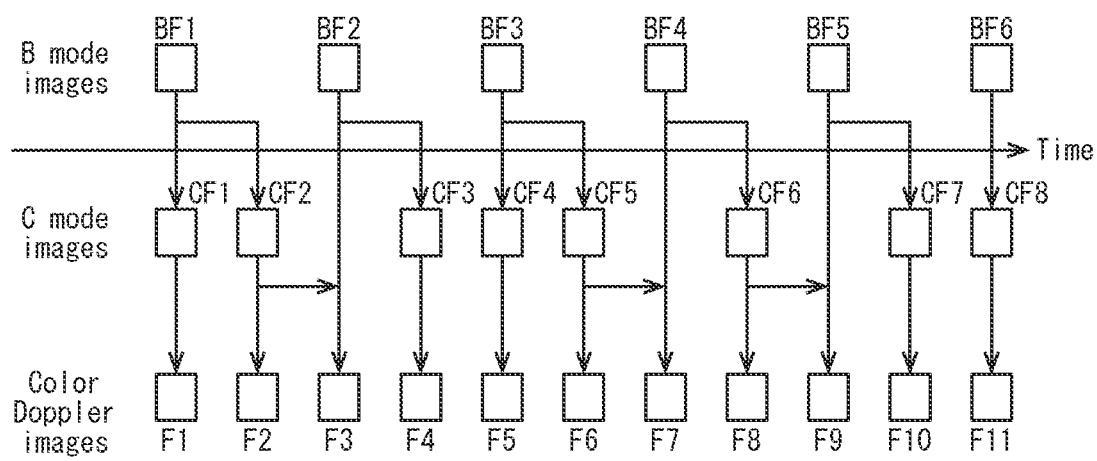
FIG. 2B is a schematic diagram illustrating image synthesis.

The image synthesizer 1073 may generate a frame of a color Doppler image when a new frame is generated in either a B mode image or a C mode image. FIG. 2B is a schematic diagram illustrating an example of frame synthesis. When a B mode image frame $BF_1$ and a C mode image frame $CF_1$ are generated, the image synthesizer 1073 superimposes the C mode image frame $CF_1$ on the B mode image frame $BF_1$ to synthesize a color Doppler image frame $F_1$. Next, when a C mode image frame $CF_2$ is generated, frame $BF_1$ of the B mode image is still the latest, and therefore a C mode image frame $CF_2$ is superimposed on the B mode image frame $BF_1$ to synthesize a color Doppler image frame $F_2$. Next, when a B mode image frame $BF_2$ is generated, frame $CF_2$ of the C mode images is still the latest, and therefore the C mode image frame $CF_2$ is superimposed on the B mode image frame $BF_2$ to synthesize a color Doppler image frame $F_3$. Next, when a C mode image frame $CF_3$ is generated, frame $BF_2$ of the B mode images is still the latest, and therefore the C mode image frame $CF_3$ is superimposed on the B mode image frame $BF_2$ to synthesize a color Doppler image frame $F_4$. Next, when a B mode image frame $BF_3$ and a C mode image frame $CF_4$ are generated, the C mode image frame $CF_4$ is superimposed on the B mode image frame $BF_3$ to synthesize a color Doppler image frame $F_5$. Next, when a C mode image frame $CF_5$ is generated, frame $BF_3$ of the B mode images is still the latest, and therefore the C mode image frame $CF_5$ is superimposed on the B mode image frame $BF_3$ to synthesize a color Doppler image frame $F_6$. Next, when a B mode image frame $BF_4$ is generated, frame $CF_5$ of the C mode images is still the latest, and therefore the C mode image frame $CF_5$ is superimposed on the B mode image frame $BF_4$ to synthesize a color Doppler image frame $F_7$. Next, when a C mode image frame $CF_6$ is generated, frame $BF_4$ of the B mode images is still the latest, and therefore the C mode image frame $CF_6$ is superimposed on the B mode image frame $BF_4$ to synthesize a color Doppler image frame $F_8$. Subsequently, when a new frame is generated for either a B mode image or C mode image, the image synthesizer 1073 superimposes the latest C mode image frame on the latest B mode image frame at that time, thereby generating a color Doppler image frame.

If frame rate of C mode images is sufficiently higher than frame rate of B mode images, the image synthesizer 1073 may be configured to generate a color Doppler image frame only when new C mode image frame is generated.

Operations

The following describes operations of the ultrasound diagnostic device 100 with the structure described above.

FIG. 6 is a flowchart illustrating operations of the ultrasound diagnostic device 100.

First, in step S100, ultrasound is transmitted and acoustic line signals are generated for all scan lines in the B-ROI. Thus, a first frame of B mode images is generated. At this time the ultrasound diagnostic device 100 may display the generated B mode image on the display 108.

Next, a B mode scan line counter i is set to 1, a C mode scan line counter j is set to 0, and a consecutive transmission counter c is set to 1 (step S201).

Then, with respect to the i-th scan line, B mode transmission and corresponding acoustic line signal generation are performed (step S202). Here, this means B mode transmission and acoustic line signal generation for a scan line B1.

Next, it is determined whether or not the value of i is less than a number $i_{max}$ of B mode scan lines (step S203). Here, i=1 and $i_{max}$=16, and therefore it is determined that i is less than $i_{max}$ ("Yes") and processing proceeds to step S207. Steps S204 to S206 are described later.

Next, it is determined whether or not the value of c is less than a number M of consecutive B mode transmissions (step S207). Here, c=1 and M=4, and therefore it is determined that c is less than M ("Yes") and processing proceeds to step S208. In step S208, i and c are incremented, then processing returns to step S202. Thus, processing of step S202 is performed for i=2 and c=2. That is, B mode transmission and acoustic line signal generation for a scan line B2 (step S202).

In the following steps S203, S207, the results are both "Yes", and therefore in step S208, i and c are incremented and processing returns to step S202. Thus, processing of step S202 is performed for i=3 and c=3. That is, B mode transmission and acoustic line signal generation for a scan line B3 (step S202).

In the following steps S203, S207, the results are both "Yes", and therefore in step S208, i and c are incremented and processing returns to step S202. Thus, processing of step S202 is performed for i=4 and c=4. That is, B mode transmission and acoustic line signal generation for a scan line B4 (step S202).

The result of the next step S203 is "Yes", and therefore processing proceeds to step S207. On the other hand, in step S207, c=4 and M=4, and therefore c is not less than M ("No"), and processing proceeds to step S301. As a result, after a B mode transmission event consisting of four B mode transmissions is performed, processing proceeds to a C mode transmission event.

Next, the C mode scan line counter j is incremented and the consecutive transmission counter c is initialized to 1 (step S301).

Then, with respect to the j-th scan line, C mode transmission and corresponding acoustic line signal generation are performed (step S302). Here, this means C mode transmission and acoustic line signal generation for a scan line C1.

Next, it is determined whether or not the value of j is less than a number $j_{max}$ of C mode scan lines (step S303). Here, j=1 and $j_{max}$=12, and therefore it is determined that j is less than $j_{max}$ ("Yes") and processing proceeds to step S307. Steps S304 to S306 are described later.

Next, it is determined whether or not the value of c is less than a number N of consecutive C mode transmissions (step S307). Here, c=1 and N=4, and therefore it is determined that c is less than N ("Yes") and processing proceeds to step S308. In step S308, j and c are incremented, then processing returns to step S302. As a result, C mode transmission and acoustic line signal generation are performed for a scan line C2 (step S302). Then, as the B mode processing described above, C mode transmission and acoustic line signal generation are performed for scan lines C3 and C4 (step S302). In step S307 directly after step S302 for scan line C4, c=4 and N=4, and therefore it is determined that c is not less than N ("No") and processing proceeds to step S309. As a result, after a C mode transmission event consisting of four C mode transmissions is performed, processing proceeds to a B mode transmission event.

In step S309, the B mode scan line counter i is incremented, and the consecutive transmission counter c is initialized to 1 (step S309). As a result, B mode transmission and acoustic line signal generation are performed for scan line B5, as a continuation from the previous B mode transmission event (step S202). Then, in the same way, after B mode transmission and acoustic line signal generation for scan lines B6, B7, and B8, C mode transmission and acoustic line signal generation are performed for scan line C5, as a continuation from the previous C mode transmission event.

In the same way, C mode transmission and acoustic line signal generation are performed for scan lines C6, C7, and C8. Then, after B mode transmission and acoustic line signal generation for scan lines B9, B10, B11, and B12, C mode transmission and acoustic line signal generation are performed for scan lines C9, C10, and C11.

After C mode transmission and acoustic line signal generation for scan line C11, C mode transmission and acoustic line signal generation are performed for scan line C12 (step S302). In step S303, j=12 and $j_{max}$=12, and therefore it is determined that j is not less than $j_{max}$ ("No") and processing proceeds to step S304.

In step S304, a C mode image is generated and an output image is generated. Specifically, velocity information is calculated by comparing acoustic lines for one frame pertaining to the latest C mode transmissions with acoustic lines corresponding to one or more previous frames, in order to generate the C mode image. Then, by superimposing the latest C mode image on the B mode image, a display image is generated and updated.

Next, whether or not there is an end instruction from a user is determined (step S305), and if there is no instruction, the C mode scan line counter j is reset to 0 (step S306), and processing proceeds to step S307. In step S307, c=4 and N=4, and therefore it is determined that c is not less than N ("No"), and processing proceeds to step S309. Accordingly, processing proceeds to a B mode transmission event.

In the next B mode transmission event, B mode transmission and acoustic line signal generation are performed for scan lines B13, B14, and B15.

After B mode transmission and acoustic line signal generation for scan line B15, B mode transmission and acoustic line signal generation are performed for scan line C1B (step S202). In step S203 immediately after, i=16 and $i_{max}$=16, and therefore it is determined that i is not less than $i_{max}$ ("No") and processing proceeds to step S204.

In step S204, a B mode image is generated and an output image is generated. Specifically, a B mode image is generated from acoustic lines of one frame pertaining to the most recent B mode transmissions. Then, by superimposing the C mode image on the latest B mode image, a display image is generated and updated.

Next, whether or not there is an end instruction from a user is determined (step S205), and if there is no instruction, the B mode scan line counter i is reset to 0 (step S206), and processing proceeds to step S207. In step S207, c=4 and M=4, and therefore it is determined that c is not less than M ("No"), and processing proceeds to step S209. Accordingly, processing proceeds to a C mode transmission event.

Brief Review

As described above, according to the ultrasound diagnostic device 100 pertaining to at least one embodiment, time division processing is performed, dividing time between B mode transmission and reception processing pertaining to generation of B mode images and C mode transmission and reception processing pertaining to generation of C mode images. As a result, B mode image frame rate and C mode image frame rate can each be kept constant and performed with an arbitrary balance. According, it is possible to improve C mode image frame rate while sacrificing B mode image frame rate, while also making it possible to secure a minimum frame rate for B mode images.

Further, according to the ultrasound diagnostic device 100, B mode transmission and reception processing for one frame are performed in advance before alternating between B mode transmission and C mode transmission according to time division. As a result, even when a B mode image frame rate is lower than a C mode image frame rate, a C mode image can be superimposed and displayed on the B mode image based on acoustic line signals acquired in advance. Accordingly, even when B mode image frame rate is low, a situation where a B mode image is not displayed can be avoided.

Modification 1

According to the ultrasound diagnostic device 100 pertaining to Embodiment 1, as illustrated in the schematic diagrams of FIG. 2A and FIG. 2B, and the time chart of FIG. 3, the number of scan lines in the B-ROI is 16, the number of scan lines in the C-ROI is 12, the number of consecutive B mode transmissions M is 4, and the number of consecutive C mode transmissions N is 4. However, the number of consecutive B mode transmissions M and the number of consecutive C mode transmissions N may be any values. Further, with respect to one B mode transmission or one C mode transmission, acoustic lines may be acquired for multiple scan lines.

According to Modification 1, the number of consecutive C mode transmissions N is defined as the number of transmissions for one frame of a C mode image. That is, N is determined so as to acquire acoustic lines for all C mode scan lines in one C mode transmission event. When acoustic lines are acquired for $n_C$ scan lines by one C mode transmission, N can be expressed as N=$j_{max}$/$n_C$. Further, when width in an element array direction of C-ROI is $W_C$ and density of scan lines in the element array direction is $d_C$, N can be expressed according to the following expression.

$$N=W_C \times d_C/n_C$$

(However, if N is not an integer, N is rounded up to an integer)

Next, the number of consecutive B mode transmissions M is set to be equal to or less than a first defined ratio with respect to N, above. When the first defined ratio is defined as $R_1$, M satisfies the following condition.

$$M \leq N \times R_1$$

Here, in order to make the C mode image frame rate equal to or greater than a reference level and improve tracking performance in blood flow visualization, it is preferable that the first defined ratio $R_1$ is less than one.

Modification 2

According to Modification 2, M and N are determined so that a pulse repetition frequency (PRF) at which ultrasound waves repeat meets a defined criteria.

When the pulse repetition frequency PRF is defined as Fc MHz, flow velocity scale is defined as s cm/s, ultrasound frequency is defined as f MHz, and ultrasound velocity in a subject is defined as v m/s, the following relationship is satisfied.

$$F_C = 4 \times 10^{4} \times s \times f/v$$

In a sequence according to Embodiment 1, acoustic lines are created one a time for all scan lines to form one frame, and therefore the pulse repetition frequency PRF for one scan line matches the C mode image frame rate. When a transmission interval time for continuous B mode transmission is defined as TIB and a transmission interval time for continuous C transmission is defined as TIC, a C mode image frame rate FRC is expressed as follows.

$$FR_C = 1/(M \times T_{IB} + N \times T_{IC})$$

Here, $F_C = FR_C$, and therefore M can be set so that the flow velocity scale s satisfies a desired condition.

Further, M is set to be equal to or greater than a second defined ratio with respect to N. When the second defined ratio is defined as $R_2$, M satisfies the following condition.

$$M \geq N \times R_2$$

Here, when M satisfies the above relationship, M is not too low, or in other words the B mode image frame rate is not too low.

Embodiment 2

According to Embodiment 1, a color Doppler image is updated every time ultrasound transmission and reception processing for one frame is completed for each B mode image or C mode image. However, when a difference between C mode image frame rate and B mode image frame rate is large, a time difference between acquisition times of B mode images and C mode images is likely to occur, and a low B mode image frame rate becomes conspicuous.

According to Embodiment 2, an apparent frame rate of B mode images is improved by changing processing pertaining to B mode image display.

Structure

According to Embodiment 2, function block structure is the same as that of Embodiment 1, but for the B mode image processor 106 and the B mode image generator 1072, processing units and timing are different.

According to Embodiment 1, the B mode image processor 106 generates a frame B signal, which is one frame worth of synthesized acoustic line signals, but according to Embodiment 2, subframe B signals are generated for each acoustic line signal obtained in a B mode transmission event. Further, the B mode image generator 1072 holds a generated B mode image, and upon receiving a subframe B signal from the B mode image processor, generates a partial B mode image and superimposes it on the B mode image held, and thereby updates only part of the B mode image corresponding to the subframe B signal. As a result, although frame rate of B mode images as a whole is not improved, a time lag from B mode transmission to B mode image updating is reduced.

Operations

Figure 8:
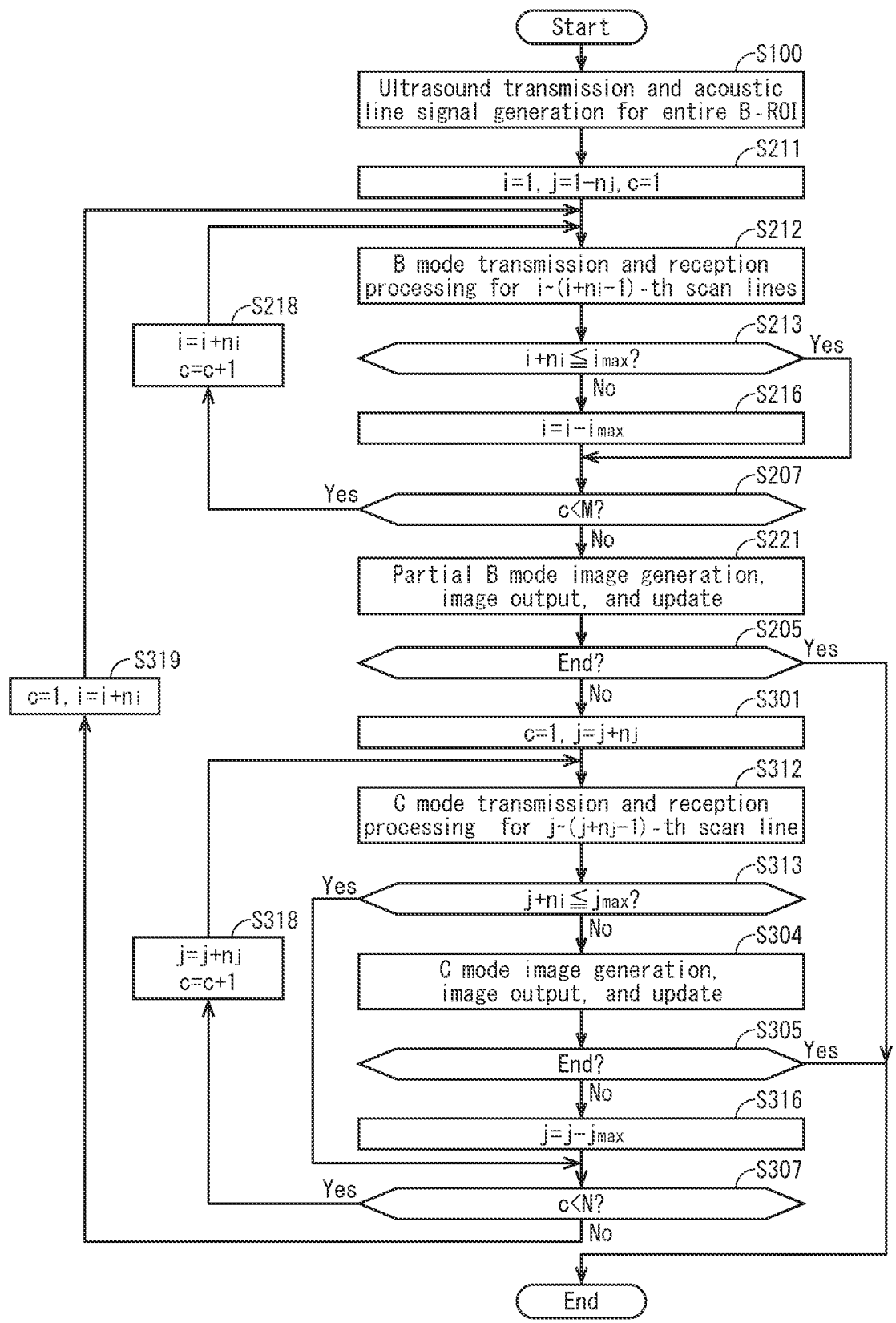
FIG. 8 is a flowchart illustrating operations of an ultrasound diagnostic device pertaining to Embodiment 2.

FIG. 8 is a flowchart illustrating operations of an ultrasound diagnostic device pertaining to Embodiment 2. In the following example, the B-ROI scan line number $i_{max}=16$, a number of scan lines for one B mode transmission $n_i=2$, the number of consecutive transmissions M=2, the C-ROI scan line number $j_{max}=12$, a number of scan lines for one C mode transmission n=2, and the number of consecutive transmissions N=6. That is, for C mode transmission, data for one frame is acquired by transmitting N time consecutively, whereas for B mode transmission, data for ¼ of a frame is acquired by transmitting M times consecutively.

First, in step S100, ultrasound is transmitted and acoustic line signals are generated for all scan lines in the B-ROI. Thus, a first frame of B mode images is generated.

Next, a B mode scan line counter i is set to 1, a C mode scan line counter j is set to $1-n_j$, and a consecutive transmission counter c is initialized to 1 (step S211).

Then, with respect to scan lines from i to $i+n_i-1$, B mode transmission and corresponding acoustic line signal generation are performed (step S212). Here, this means B mode transmission and acoustic line signal generation for scan lines B1 and B2.

Next, it is determined whether or not the value of $i+n_i$ is equal to or less than the number $i_{max}$ of B mode scan lines (step S213). Here, i=1, $n_i=2$, and $i_{max}=16$, and therefore it is determined that the value of $i+n_i$ is equal to or less than $i_{max}$ ("Yes"), and processing proceeds to step S207. When the result of step S213 is "No", $i_{max}$ is subtracted from i to proceed to the next processing loop (S216).

Next, it is determined whether or not the value of c is less than a number M of consecutive B mode transmissions (step S207). Here, c=1 and M=2, and therefore it is determined that c is less than M ("Yes") and processing proceeds to step S218. In step S218, i is incremented by n, and c is incremented by 1, then processing returns to step S212. Thus, processing of step S212 is performed for i=3 and c=2.

Then, with respect to scan lines from i to $i+n_i-1$, B mode transmission and corresponding acoustic line signal generation are performed (step S212). Here, this means B mode transmission and acoustic line signal generation for scan lines B3 and B4.

Next, it is determined whether or not the value of $i+n_i$ is equal to or less than the number $i_{max}$ of B mode scan lines (step S213). Here, i=3, m=2, and $i_{max}=16$, and therefore it is determined that the value of $i+n_i$ is equal to or less than $i_{max}$ ("Yes"), and processing proceeds to step S207.

Next, it is determined whether or not the value of c is less than the number M of consecutive B mode transmissions (step S207). Here, c=2 and M=2, and therefore it is determined that c is not less than M ("No") and processing proceeds to step S221.

In step S221, a partial B mode image is generated and an output image is generated. Specifically, a partial B mode image is generated from a subframe B signal obtained in response to the B mode transmission event, that is, the subframe B signal corresponding to scan line B1, B2, B3, B4. Here, a B mode image is generated in which areas corresponding to scan lines B1 to B4 have 0% transparency (opaque) and other areas corresponding to scan lines B5 to B16 have 100% transparency (completely transparent), and the B mode image is superimposed on the previously generated B mode image. As a result, a B mode image is generated in which only an area corresponding to scan lines B1 to B4 is updated. Then, by superimposing the C mode image on the latest B mode image, a display image is generated and updated.

Next, whether or not there is an end instruction from a user is determined (step S205), and if there is no such instruction, processing proceeds to step S301. Accordingly, processing proceeds to C mode transmission.

Next, the C mode scan line counter j is incremented and the consecutive transmission counter c is initialized to 1 (step S301).

Then, with respect to scan lines from j to $j+n_j-1$, C mode transmission and corresponding acoustic line signal generation are performed (step S312). Here, this means C mode transmission and acoustic line signal generation for scan lines C1 and C2.

Next, it is determined whether or not the value of $j+n_j$ is equal to or less than the number $j_{max}$ of C mode scan lines (step S313). Here, $j=1$, $n_j=2$, and $j_{max}=12$, and therefore it is determined that the value of $j+n_j$ is equal to or less than $j_{max}$ ("Yes"), and processing proceeds to step S307.

Next, it is determined whether or not the value of c is less than the number N of consecutive C mode transmissions (step S307). Here, $c=1$ and $N=6$, and therefore it is determined that c is less than N ("Yes") and processing proceeds to step S318. In step S318, j is incremented by $n_j$ and c is incremented by 1, then processing returns to step S312. Then, in a second C mode transmission, C mode transmission and acoustic line signal generation are performed for scan lines C3 and C4. Similarly, C mode transmission and acoustic line signal generation is performed for scan lines C5 and C6 in a third C mode transmission, for scan lines C7 and C8 in a fourth C mode transmission, for scan lines C9 and C10 in a fifth C mode transmission, and for scan lines C11 and C12 in a sixth C mode transmission (step S312). In the sixth C mode transmission, in step S313, $j=11$, $n_j=2$, and $j_{max}=12$, and therefore it is determined that $j+n_j$ is not equal to or less than $j_{max}$ ("No"), and processing proceeds to step S304.

In step S304, a C mode image is generated and an output image is generated. Specifically, the C mode image is generated from a frame CFM signal obtained in response to one frame worth of C mode transmissions. Then, by superimposing the latest C mode image on the B mode image, a display image is generated and updated.

Next, whether or not there is an end instruction from a user is determined (step S305), and if there is no such instruction, $j_{max}$ is subtracted from the C mode scan line counter j (step S316), and processing proceeds to step S307. In step S307, $c=6$ and $N=6$, and therefore it is determined that c is not less than N ("No"), and processing proceeds to step S319. Accordingly, processing proceeds to a B mode transmission event.

Brief Review

Figure 7A:
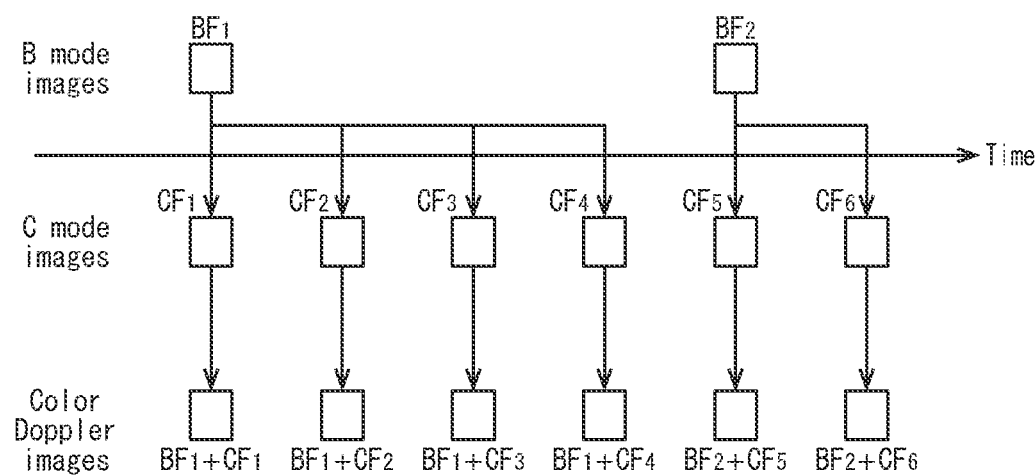
FIG. 7A and FIG. 7B are schematic diagrams pertaining to Embodiment 1 and Embodiment 2, respectively, illustrating image synthesis target frames when a ratio of frame rates is 1:4 for B mode image frame rate to C mode image frame rate.
Figure 7B:
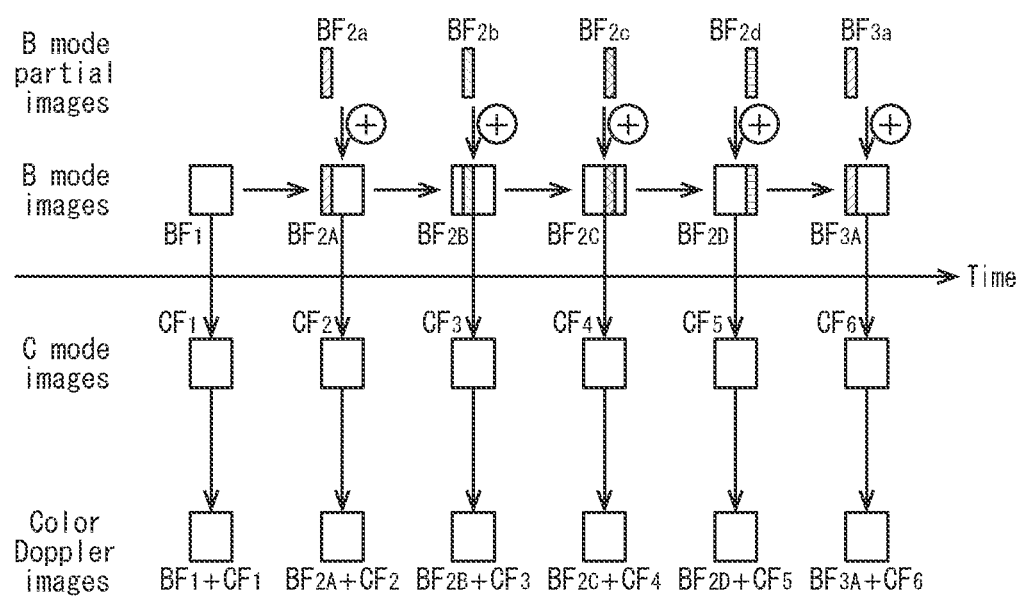

As described above, according to the ultrasound diagnostic device 100 pertaining to at least one embodiment, a B mode image is partially updated every time M consecutive B mode transmissions are completed. Specifically, according to Embodiment 1, as illustrated in the schematic diagram of FIG. 7A, when a ratio of B mode image frame rate to C mode image frame rate is 1:4, B mode images are not updated until four frames of C mode images are updated, but according to Embodiment 2, as illustrated in the schematic diagram of FIG. 7B, B mode images are partially updated at the same time as C mode images. Accordingly, even when B mode image frame rate is low, B mode images are partially updated, and therefore a time lag between B mode transmission and B mode image display can be reduced, and usability can be improved.

Modification 3

According to Modification 3, the number of consecutive C mode transmissions N is determined so that a time required for a C mode transmission event is equal to or less than a defined reference. According to Embodiment 2, a B mode transmission event and corresponding partial update of a B mode image are performed between C mode transmission events. That is, a C mode transmission event is performed between B mode transmission events and corresponding B mode image partial updates. Accordingly, if a time required for a C mode transmission event is too long, a time lag between B mode image partial updates becomes large, making seam line artifacts more likely to become apparent and decreasing B mode image quality. Therefore, when an upper limit of time required for a C mode transmission event is a defined reference value $\Delta T$ and a transmission interval time for consecutive C mode transmission with a C mode transmission event is $T_{IC}$, N can be defined as follows.

$$N=[\Delta T/T_{IC}]$$

However, [x] is the largest integer that does not exceed x.

Next, the number of consecutive B mode transmissions M is set so that a time required for a B mode transmission event is equal or less than a third defined ratio with respect to time required for a C mode transmission event. When the time required for a B mode transmission event is $T_{TB}$ and a time required for a C mode transmission event is $T_{TC}$, the transmission interval time for B mode transmission $T_{IB}$ and the transmission interval time for C mode transmission $T_{IC}$ can be used as follows.

$$T_{TB}=M \times T_{IB}$$

$$T_{TC}=N \times T_{IC}$$

Here, when the third defined ratio is defined as $R_3$, the following expression can be established.

$$T_{TB} \leq T_{TC} \times R_3$$

Accordingly, substituting the two previous expressions into the above expression, the following relationship can be established.

$$N \leq N \times (T_{IC}/T_{IB}) \times R_3$$

Modification 4

According to Modification 4, M and N are determined so that a pulse repetition frequency PRF at which ultrasound waves repeat meets a defined criteria.

N is determined as determined according to Modification 3.

In a sequence according to Embodiment 2, acoustic lines are created one time for all scan lines to form one frame, and therefore the pulse repetition frequency PRF for one scan line matches the C mode image frame rate FRc. When a width in the element array direction of the C-ROI is $W_c$, density of scan lines in the element array direction is $d_c$, and a number of scan lines for which acoustic lines are acquired by one C mode transmission is $n_c$, then a C mode transmission number for one frame $Tx_c$, can be expressed as follows.

$$Tx_C = W_C \times d_C / n_C$$

(However, if $Tx_C$ is not an integer, $Tx_C$ is rounded up to an integer)

Accordingly, a number of C mode transmission events per frame $B_C$ can be expressed as follows.

$$B_C = Tx_C / N$$

(However, if $B_C$ is not an integer, $B_C$ is rounded up to an integer)

Accordingly, a C mode image frame rate $FR_C$ can be expressed as follows.

$$FR_C = 1 / \{(T_{TB} + T_{TC}) \times B_c\}$$
$$= 1 / \{(M \times T_{IB} + N \times T_{IC}) \times B_c\}$$

Accordingly, by substituting $FR_C$=PRF into the above expression and solving for M, the number of consecutive B mode transmissions M, which is a setting target, can be obtained.

Further, the time required for a B mode transmission event is set to be equal to or greater than a fourth defined ratio with respect to the time required for a C mode transmission event. That is, when the fourth defined ratio is defined as $R_4$, whether or not the following expression holds true is determined.

$$T_{TB} \geq T_{TC} \times R_4$$

Here, when M satisfies the above relationship, M is not too low, or in other words the B mode image frame rate is not too low.

Embodiment 3

According to Embodiment 1 and Embodiment 2, acoustic lines are generated for the same number of scan lines for all C mode transmissions for C mode images, and N C mode transmissions are always performed consecutively in one C mode transmission event. However, if a total number of scan lines in the C-ROI is not an integer multiple of the number of scan line scanned by one C mode transmission event, a problem arises in that the pulse repetition frequency (PRF) is not constant.

Figure 9:
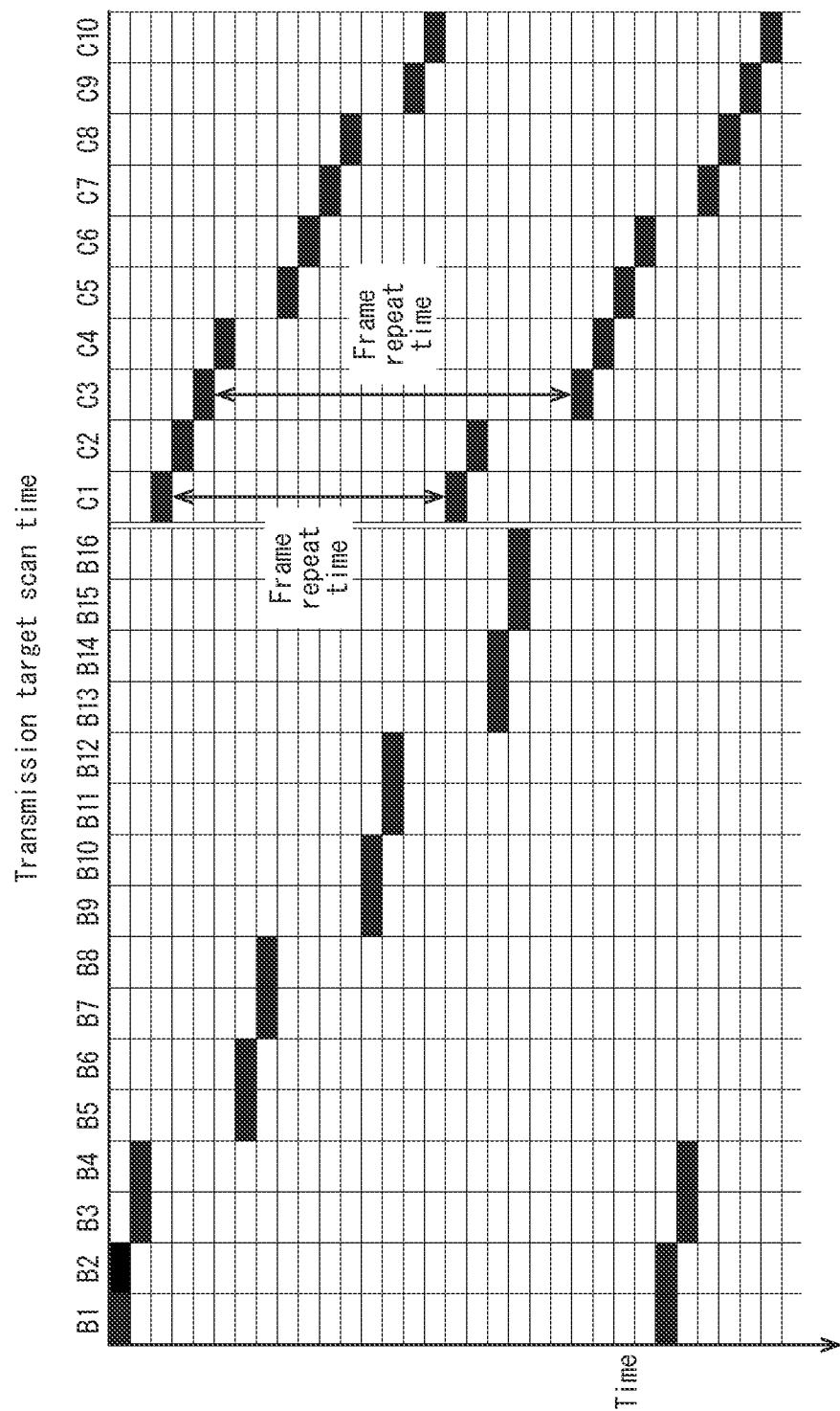
FIG. 9 is a time chart pertaining to Embodiment 2 when a total number of C-ROI scan lines is not an integer multiple of the number of scan lines scanned by one C mode transmission event.

FIG. 9 is a time chart illustrating a case where a total number of C-ROI scan lines is not an integer multiple of the number of scan lines scanned by one C mode transmission event. In this example, the number of scan lines scanned by one C mode transmission event is four, while the total number of scan lines in the C-ROI is ten. Accordingly, as illustrated in FIG. 9, in the third C mode transmission event, transmission is performed across a first frame and a second frame of C mode images. Further, positions of scan lines that separate C mode transmission events are different between the first frame and the second frame. Accordingly, in such a case, the number of B mode transmissions inserted between C mode transmissions varies depending on spatial position of scan line and frame number, and therefore pulse repetition frequency (PRF) is not constant, spatially or temporally. For example, with respect to scan line C1, two B mode transmission events are inserted between C mode transmissions, and with respect to scan line C3, three B mode transmission events are inserted. Velocity detection processing and accuracy in C mode image generation depend on PRF, and therefore if PRF is not constant, calculation becomes complex and accuracy varies depending on scan line position in a C mode image, and this can cause C mode image quality deterioration.

According to Embodiment 3, PRF is made constant in C mode images, and C mode image quality is kept constant.

Operations

According to Embodiment 3, function block structure is the same as that of Embodiment 1 or Embodiment 2, but inter-frame processing is different for C mode transmission.

Figure 10:
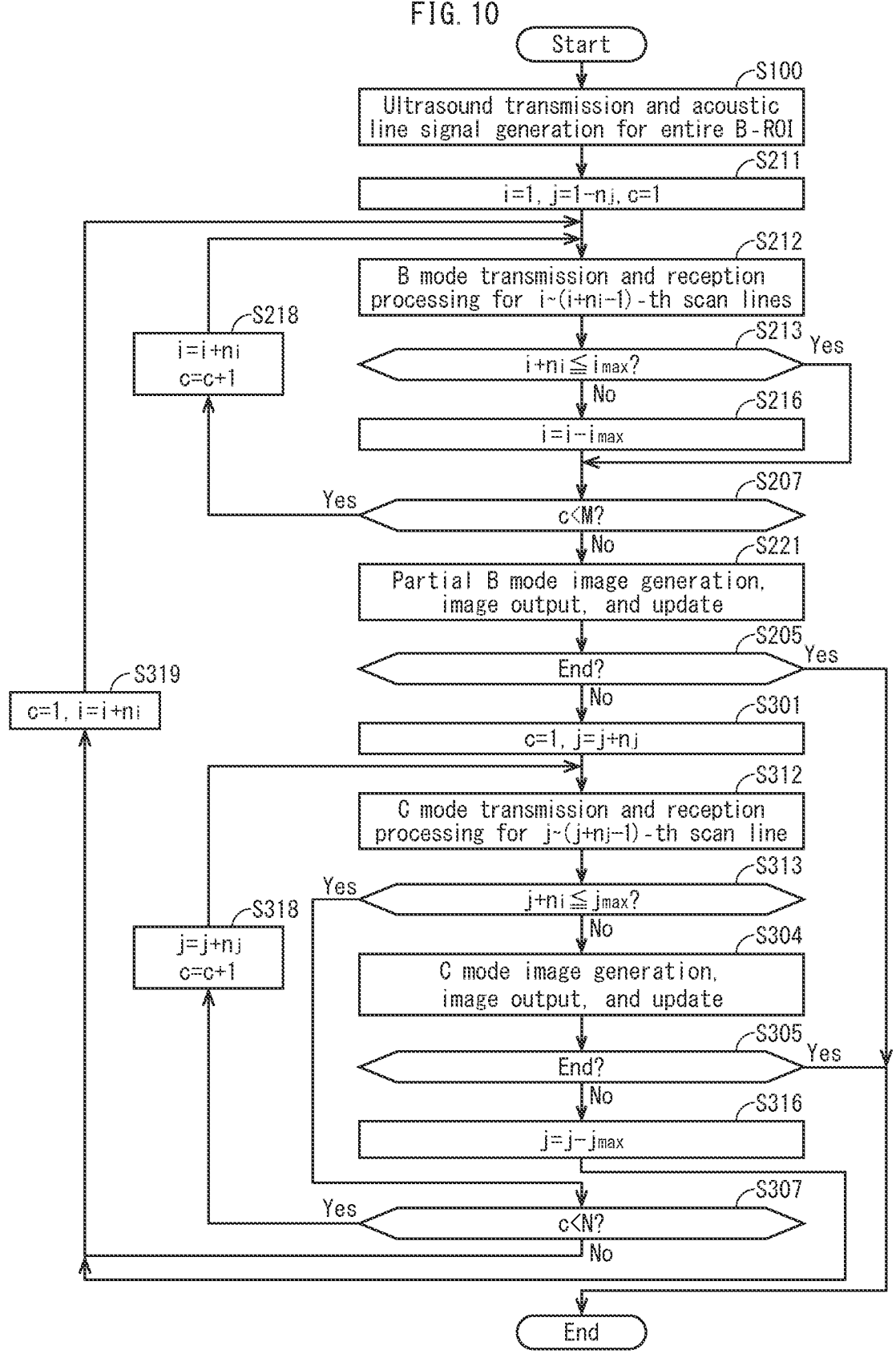
FIG. 10 is a flowchart illustrating operations of an ultrasound diagnostic device pertaining to Embodiment 3.

FIG. 10 is a flowchart illustrating operations of an ultrasound diagnostic device pertaining to Embodiment 3. In the following example, the B-ROI scan line number $i_{max}$=16, a number of scan lines for one B mode transmission $n_i$=2, the number of consecutive transmissions M=2, the C-ROI scan line number $j_{max}$=10, a number of scan lines for one C mode transmission $n_j$=1, and the number of consecutive transmissions N=4. That is, data for one C mode image frame can be acquired by 2.5 C mode transmission events.

First, in step S100, ultrasound is transmitted and acoustic line signals are generated for all scan lines in the B-ROI. Thus, a first frame of B mode images is generated.

Next, a B mode scan line counter i is set to 1, a C mode scan line counter j is set to $1-n_j$, and a consecutive transmission counter c is initialized to 1 (step S211).

Then, with respect to scan lines from i to $i+n_i-1$, B mode transmission and corresponding acoustic line signal generation are performed (step S212). Here, this means B mode transmission and acoustic line signal generation for scan lines B1 and B2.

Next, it is determined whether or not the value of $i+n_i$ is equal to or less than the number $i_{max}$ of B mode scan lines (step S213). Here, i=1, $n_i$=2, and $i_{max}$=16, and therefore it is determined that the value of $i+n_i$ is equal to or less than $i_{max}$ ("Yes"), and processing proceeds to step S207. When the result of step S213 is "No", $i_{max}$ is subtracted from i to proceed to the next processing loop (S216).

Next, it is determined whether or not the value of c is less than the number M of consecutive B mode transmissions (step S207). Here, c=1 and M=2, and therefore it is determined that c is less than M ("Yes") and processing proceeds to step S218. In step S218, i is incremented by n, and c is incremented by 1, then processing returns to step S212. Thus, processing of step S212 is performed for i=3 and c=2.

Then, with respect to scan lines from i to $i+n_i-1$, B mode transmission and corresponding acoustic line signal generation are performed (step S212). Here, this means B mode transmission and acoustic line signal generation for scan lines B3 and B4.

Next, it is determined whether or not the value of $i+n_i$ is equal to or less than the number $i_{max}$ of B mode scan lines (step S213). Here, i=3, m=2, and $i_{max}$=16, and therefore it is determined that the value of $i+n_i$ is equal to or less than $i_{max}$ ("Yes"), and processing proceeds to step S207.

Next, it is determined whether or not the value of c is less than the number M of consecutive B mode transmissions (step S207). Here, c=2 and M=2, and therefore it is determined that c is not less than M ("No") and processing proceeds to step S221.

In step S221, a partial B mode image is generated and an output image is generated. Here, a B mode image is generated in which areas corresponding to scan lines B1 to B4 have 0% transparency (opaque) and other areas corresponding to scan lines B5 to B16 have 100% transparency (completely transparent), and the B mode image is superimposed on the previously generated B mode image. As a result, a B mode image is generated in which only an area corresponding to scan lines B1 to B4 is updated. Then, by superimposing the C mode image on the latest B mode image, a display image is generated and updated.

Next, whether or not there is an end instruction from a user is determined (step S205), and if there is no such instruction, processing proceeds to step S301. Accordingly, processing proceeds to C mode transmission.

Next, the C mode scan line counter j is incremented and the consecutive transmission counter c is initialized to 1 (step S301).

Then, with respect to scan lines from j to $j+n_{j-1}$, C mode transmission and corresponding acoustic line signal generation are performed (step S312). Here, this means C mode transmission and acoustic line signal generation for scan line C1.

Next, it is determined whether or not the value of $j+n_j$ is equal to or less than the number $j_{max}$ of C mode scan lines (step S313). Here, $j=1$, $n_j=1$, and $j_{max}=10$, and therefore it is determined that the value of $j+n_j$ is equal to or less than $j_{max}$ ("Yes"), and processing proceeds to step S307.

Next, it is determined whether or not the value of c is less than the number N of consecutive C mode transmissions (step S307). Here, $c=1$ and $N=4$, and therefore it is determined that c is less than N ("Yes") and processing proceeds to step S318. In step S318, j is incremented by $n_j$ and c is incremented by 1, then processing returns to step S312. Then, in a second C mode transmission, C mode transmission and acoustic line signal generation are performed for scan line C2. Similarly, in a third C mode transmission, C mode transmission and acoustic line signal generation are performed for scan line C3 (step S312). In a fourth C mode transmission, in step S313, $j=4$, $n_j=1$, and $j_{max}=10$, and therefore it is determined that $j+n_j$ is equal to or less than $j_{max}$ ("Yes"), and processing proceeds to step S307.

Next, it is determined whether or not the value of c is less than the number N of consecutive C mode transmissions (step S307). Here, $c=4$ and $N=4$, and therefore it is determined that c is not less than N ("No") and processing proceeds to step S319. Accordingly, after the fourth C mode transmission, processing proceeds to B mode transmission.

In step S319, the B mode scan line counter i is incremented by $n_i$, and the continuous transmission counter c is initialized to 1 (step S319). As a result, B mode transmission and acoustic line signal generation are performed for scan lines B5 and B6, as a continuation from the previous B mode transmission event (step S212). Then, in the same way, after B mode transmission and acoustic line signal generation for scan lines B7 and B8, C mode transmission and acoustic line signal generation are performed for scan line C5, as a continuation from the previous C mode transmission event.

In the same way, C mode transmission and acoustic line signal generation are performed for scan lines C6, C7, and C8. Then, after B mode transmission and acoustic line signal generation for scan lines B9, B10, B11, and B12, C mode transmission and acoustic line signal generation are performed for scan line C9.

Then C mode transmission and acoustic line signal generation are performed for scan line C10 (step S312). In step S313 immediately after, $j=10$, $n_j=1$, and $j_{max}=10$, and therefore it is determined that $j+n_j$ is not equal to or less than $j_{max}$ ("No"), and processing proceeds to step S304.

In step S304, a C mode image is generated and an output image is generated. Specifically, velocity information is calculated by comparing acoustic lines for one frame pertaining to the latest C mode transmissions with acoustic lines corresponding to one or more previous frames, in order to generate the C mode image. Then, by superimposing the latest C mode image on the B mode image, a display image is generated and updated.

Next, whether or not there is an end instruction from a user is determined (step S305), and if there is no such instruction, $j_{max}$ is subtracted from the C mode scan line counter j (step S316), and processing proceeds to step S319. That is, in C mode transmission, when one frame worth of transmission is completed, even if consecutive C mode transmission has not completed N times, processing proceeds to B mode transmission.

Brief Review

Figure 11:
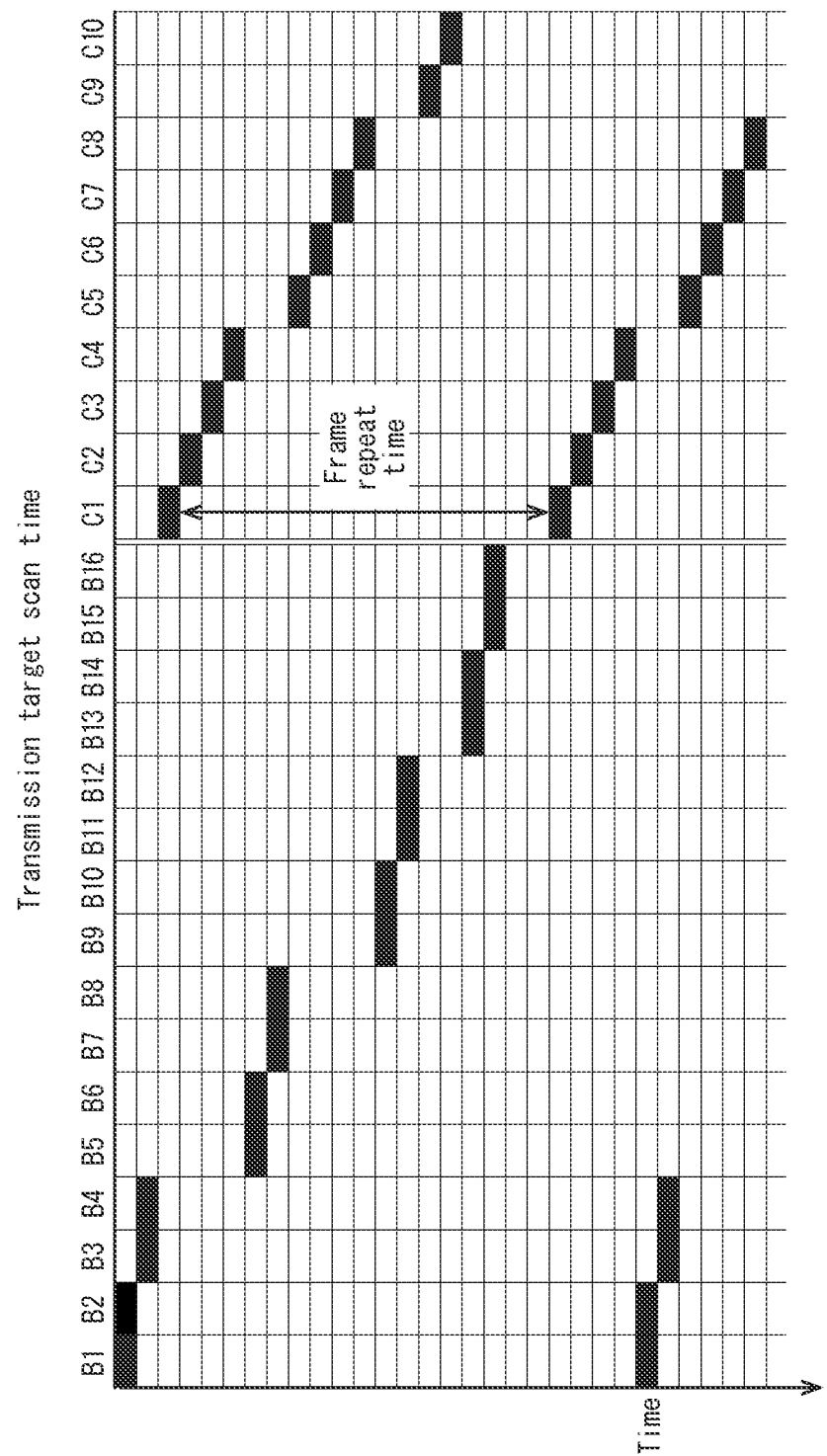
FIG. 11 is a time chart pertaining to Embodiment 3 when a total number of C-ROI scan lines is not an integer multiple of the number of scan lines scanned by one C mode transmission event.

As described above, according to the ultrasound diagnostic device 100 pertaining to at least one embodiment, when one frame worth of transmission is completed for C mode transmission, then even if a C mode transmission event is not completed, the remaining C mode transmission is not performed and B mode transmission is started. Accordingly, as illustrated in the time chart of FIG. 11, a repeat rate of C mode transmission with respect to any given scan line is constant, or in other words, the PRF is constant. Accordingly, C mode image quality can be made uniform both spatially and temporally.

Embodiment 4

According to Embodiments 1-3, a focused wave is transmitted and acoustic line generated on a scan line for each B mode transmission and each C mode transmission. However, for example, in one or both of B mode transmission and C mode transmission, transmission using a non-converging wave such as a plane wave may be performed, and acoustic line synthesis may be performed based on transmission in different transmission directions.

Figure 12A:
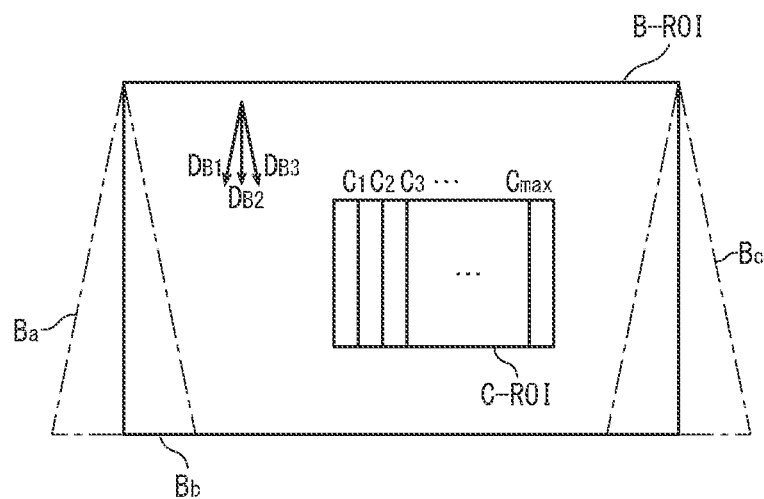
FIG. 12A and FIG. 12B are schematic diagrams illustrating target regions for ultrasound transmission and reception in B mode transmission and C mode transmission, pertaining to Embodiment 4.

Specifically, for example, for B mode transmission, multiple transmissions having different transmission directions, such as in spatial compounding, may be performed to generate an acoustic line signal. FIG. 12A illustrates an example of generating a B mode image by plane wave transmission in different transmission directions. By transmitting a plane wave in a first direction $D_{B1}$ to generate acoustic line signals for observation points in an area Ba, transmitting a plane wave in a second direction $D_{B2}$ to generate acoustic line signals for observation points in an area Bb, and transmitting a plane wave in a third direction $D_{B3}$ to generate acoustic line signals for observation points in an area $B_C$, and synthesizing, a B mode image is generated for the B-ROI. Here, one B mode transmission corresponds to transmission of a plane wave in one direction and corresponding acoustic line signal generation, and one frame of B mode transmission refers to B mode transmission in all directions. That is, one B mode transmission corresponds to plane wave transmission in one of the first direction $D_{B1}$, the second direction $D_{B2}$, or the third direction $D_{B3}$, and corresponding acoustic line signal generation, and one frame of B mode transmission corresponds to plane wave transmission once for each of the first direction $D_{B1}$, the second direction $D_{B2}$, and the third direction $D_{B3}$, and corresponding acoustic line signal generation. Further, for example, in a case of B mode transmission in which plane waves are transmitted in five directions and B mode transmission is performed twice in succession, transmission may be performed in the order of B mode transmission in a first direction, B mode transmission in a second direction, C mode transmission N times, B mode transmission in a third direction, B mode transmission in a fourth direction, C mode transmission N times, B mode transmission in a fifth direction, B mode transmission in the first direction, C mode transmission N times, and so on. In generating a partial B mode image, when transmitting plane waves in five directions, for example, synthesis of acoustic lines signals pertaining to the latest five B mode transmissions can be used. In B mode transmission for a first frame, B mode transmission is performed in all directions and corresponding acoustic line signals are generated.

Figure 12B:
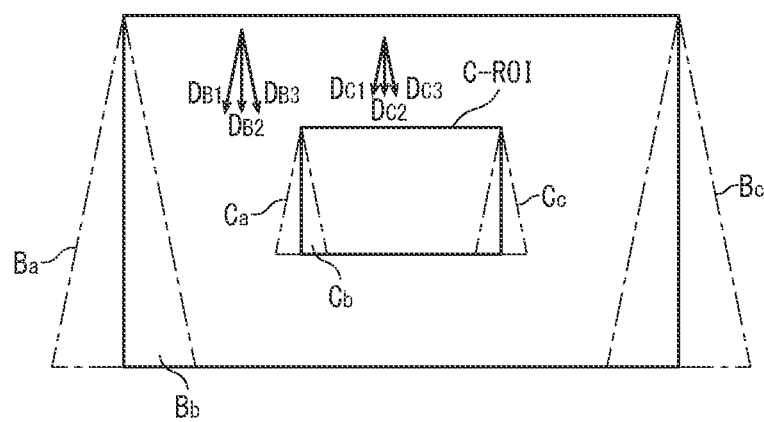

Further, as illustrated in FIG. 12B, in addition to B mode transmission, plane waves may be transmitted in three directions for C mode transmission, and acoustic line signals may be generated by synthesis. FIG. 12B illustrates a case in which acoustic line signals for observation points in an area Ca are generated by plane wave transmission in a first direction $D_{C1}$, acoustic line signals for observation points in an area Cb are generated by plane wave transmission in a second direction $D_{C2}$, acoustic line signals for observation points in an area Cc are generated by plane wave transmission in a third direction $D_{C3}$, and synthesis of these generates C mode images for the C-ROI. As a method of calculating velocity, velocity in the first direction is calculated by comparing acoustic line signals obtained by two consecutive transmissions of plane waves in the first direction $D_{C1}$, velocity in the second direction is calculated by comparing acoustic line signals obtained by two consecutive transmissions of plane waves in the second direction $D_{C2}$, and velocity in the third direction is calculated by comparing acoustic line signals obtained by two consecutive transmissions of plane waves in the third direction $D_{C3}$, and for each observation point, velocity at the observation point can be calculated by vector synthesis of the velocity in the first direction, the velocity in the second direction, and the velocity in the third direction.

Modification 5

According to Modification 5, C mode transmission is performed by plane wave, and B mode transmission is performed by focused wave as in Embodiment 1. Even in this case, the B mode image may be generated by a spatial compound. That is, a frame B signal can be generated corresponding to transmission and reception in three different directions and synthesis to generate B mode images.

The number of consecutive C mode transmissions N is defined as the number of transmissions for one frame of a C mode image. When performing plane wave C mode transmission, plane waves are transmitted in all directions by C mode transmission N times. When a plane wave transmission direction in C mode transmission is $D_C$, the number of consecutive transmissions N and the number of C mode transmissions per frame $Tx_C$ can be expressed as follows.

$$N = Tx_c = D_C$$

The number of consecutive B mode transmissions M is set so that a B mode image frame rate $FR_B$ is equal to or less than a fifth defined ratio $R_5$ with respect to a C mode image frame rate $FR_C$. A time for transmission and reception of one frame of C mode images is shown as follows using the consecutive C mode transmission interval time $T_{IC}$.

$$FT_C = T_{IC} \times Tx_c$$
$$= T_{IC} \times N$$

Here, the C mode image frame rate $FR_C$ is the reciprocal of the sum of the time required $T_{TB}$ for B mode transmission M times and the time required $T_{TC}$ for C mode transmission N times. Accordingly, using $T_{TB}$, $T_{TC}$, the consecutive B mode transmission interval time $T_{IB}$, and the consecutive C mode transmission interval time $T_{IC}$, the following expression is possible.

$$FR_C = 1/(T_{TB} + T_{TC})$$
$$= 1/(M \times T_{IB} + N \times T_{IC})$$

Here, when width of the B-ROI in the array direction is $W_B$, density of scan lines in the array direction is $d_B$, and the number of scan lines for acquiring an acoustic line by one B mode transmission is $n_B$, the number of B mode transmissions for one frame $Tx_B$ is expressed as follows.

$$Tx_B = W_{IB} \times d_B/n_B$$

(However, if $Tx_B$ is not an integer, $Tx_B$ is rounded up to an integer)

Accordingly, a time required for one frame of B mode transmission $FT_B$ can be expressed as follows.

$$FT_B = T_{IB} \times Tx_B$$

Here, when a number of frames of C mode transmission between one frame of B mode images is $n_C$, the number of C mode transmissions is $BF_C$, and required time is $BT_C$, the following relationship can be established.

$$BT_C = T_{IC} \times BF_C$$
$$= T_{IC} \times N \times n_C$$

Here, one frame of C mode transmission is performed for every M B mode transmissions, and therefore the following relationship is established.

$$n_C = FT_B/M$$

Accordingly, the following expression is established.

$$BT_C = T_{IC} \times N \times FT_B/M$$

The B mode image frame rate FRB is the reciprocal of the sum of the time required for one frame of B mode transmission $FT_B$ and the time required for $n_C$ frames of C mode transmission $BT_C$. According, the following expressions can be established.

$$FR_B = 1/(FT_B + BT_C)$$
$$= 1/(T_{IB} \times Tx_B + T_{IC} \times N \times FT_B/M)$$

The number of consecutive B mode transmissions M is set so that the B mode image frame rate $FR_B$ is equal to or less than a fifth defined ratio $R_5$ with respect to the C mode image frame rate $FR_C$.

$$FR_B \leq FR_C \times R_5$$

M is set to satisfy all of the above expressions.

Modification 6

According to Modification 6, M and N are determined so that a pulse repetition frequency PRF at which ultrasound waves repeat meets a defined criteria.

According to Modification 5, the reciprocal of a time interval for transmitting a plane wave in the same direction in two consecutive C mode frames is the PRF. Accordingly, the C mode image frame rate $FR_C$ matches the PRF.

Accordingly, M can be set for a desired PRF so as to satisfy the following expression.

$$PRF=FR_C=1/(M \times T_{IB}+N \times T_{IC})$$

Further, the number of consecutive B mode transmissions M is set so that the B mode image frame rate FRB is equal to or more than a sixth defined ratio $R_5$ with respect to the C mode image frame rate $FR_C$.

$$FR_B \geq FR_C \times R_6$$

Here, when M satisfies the above relationship, M is not too low, or in other words the B mode image frame rate is not too low.

Other Modifications Pertaining to Embodiments (1) According to Embodiment 1, B mode images are updated per frame, and according to Embodiment 2, B mode images are updated after every M B mode transmissions. However, for example, B mode image frame rate may be improved by using motion compensation, motion prediction, or the like. For example, if there is a delay (time lag) of B mode frame repeat time between B mode image generation and display, motion compensation can be performed using the generated B mode image and the B mode image being displayed, and B mode image frame rate can be improved by outputting an intermediated B mode image along with an update of a C mode image. Further, for example, a B mode image processor may perform motion prediction from past frames including a latest B mode image, generate a B mode image predictive frame, and output the B mode image predictive frame along with an update of a C mode image. With such a configuration, B mode images can be updated at a higher frame rate than that of B mode transmission.

(2) According to at least one embodiment and at least one modification, the C mode image processor 105 generates a color Doppler image that maps velocity at each observation point, but may generate a power Doppler image that maps power values at each observation point based on signal strength of blood flow information at each observation point.

(3) According to at least one embodiment and at least one modification, B mode transmission and C mode transmission respectively transmit focused ultrasound having different focal points and generate acoustic lines for observation points on corresponding scan lines, or transmit plane waves in different transmission directions and generate acoustic lines for observation points in a corresponding target area. However, B mode transmission and C mode transmission are not limited to these examples, and as long as frames of B mode images and C mode images are generated by multiple ultrasound transmissions, any method may be used. For example, tissue harmonics imaging (THI) may be used, in which a first transmission and a second transmission with a phase inverted from the first transmission are each regarded as one transmission. Further, for example, when a synthetic aperture method is used, a transmission corresponding to one transmission aperture may be regarded as one transmission, and one frame of transmissions may be regarded as a plurality of transmissions corresponding to all transmission apertures.

Further, each of B mode transmission and C mode transmission may include a dummy transmission in which only a detection wave is transmitted and an acoustic line signal is not generated. In this case, the dummy transmission may also be handled as one transmission. By setting a first transmission of a B mode transmission event and/or a C mode transmission event as a dummy transmission, acoustic line signal quality deterioration due to the influence of reflected ultrasound from outside the ROI with respect to an immediately preceding ultrasound transmission can be suppressed.

(4) According to at least one embodiment and at least one modification, a combination of B mode images and C mode images is used as an example, but as long as two or more types of image are generated using time division by the same ultrasound probe, superimposed, and output as a moving image composed of a plurality of frames of each type, then there is no limitation to the combination of B mode images and C mode images, and any combination of images may be used.

(5) The present disclosure is based on the embodiments above, but the present disclosure is not limited to these embodiments, and the following examples are also included in the scope of the present disclosure.

For example, the present disclosure may include a computer system including a microprocessor and a memory, the memory storing a computer program and the microprocessor operating according to the computer program. For example, the present disclosure may include a computer system that operates (or instructs operation of connected elements) according to a computer program of a diagnostic method of an ultrasound diagnostic device of the present disclosure.

Further, examples in which all or part of the ultrasound diagnostic device, or all or part of a beamforming section are constituted by a computer system including a microprocessor, a storage medium such as read-only memory (ROM), random-access memory (RAM), etc., a hard disk unit, and the like, are included in the present disclosure. A computer program for achieving the same operations as the devices described above may be stored in RAM or a hard disk unit. The microprocessor operating according to the computer program, thereby realizing the functions of each device.

Further, all or part of the elements of each device may be configured as one system large scale integration (LSI). A system LSI is an ultra-multifunctional LSI manufactured by integrating a plurality of elements on one chip, and more specifically is a computer system including a microprocessor, ROM, RAM, and the like. The plurality of elements can be integrated on one chip, or a portion may be integrated on one chip. Here, LSI may refer to an integrated circuit, a system LSI, a super LSI, or an ultra LSI, depending on the level of integration. A computer program for achieving the same operation as the devices described above may be stored in the RAM. The microprocessor operates according to the computer program, the system LSI thereby realizing the functions. For example, a case of the beamforming method of the present disclosure stored as a program of an LSI, the LSI inserted into a computer, and a defined program (beamforming method) being executed is also included in the present disclosure.

Note that methods of circuit integration are not limited to LSI, and implementation may be achieved by a dedicated circuit or general-purpose processor. After LSI manufacture, a field programmable gate array (FPGA) or a reconfigurable processor, in which circuit cell connections and settings in the LSI can be reconfigured, may be used.

Further, if a circuit integration technology is introduced that replaces LSI due to advances in semiconductor technology or another derivative technology, such technology may of course be used to integrate the function blocks.

Further, all or part of the functions of an ultrasonic diagnostic device pertaining to at least one embodiment may be implemented by execution of a program by a processor such as a CPU. The ultrasound transmission and reception method and/or image processing method of the ultrasound diagnostic device may be realized as a non-transitory computer-readable storage medium on which a program is stored that causes execution of the ultrasound transmission and reception method and/or image processing method. A program and signals may be recorded and transferred on a storage medium so that the program may be executed by another independent computer system, or the program may of course be distributed via a transmission medium such as the Internet.

Alternatively, elements of the ultrasound diagnostic device pertaining to at least one embodiment may be implemented by a programmable device such as a CPU, a graphics processing unit (GPU), a processor, or the like, and software. This may be referred to as general-purpose computing on a graphics processing unit (GPGPU). These components can each be a single circuit component or an assembly of circuit components. Further, a plurality of components can be combined into a single circuit component or can be an aggregate of a plurality of circuit components.

According to the ultrasound diagnostic device pertaining to at least one embodiment, the ultrasound diagnostic device includes a data storage as a storage device. However, the storage device is not limited to this example and a semiconductor memory, hard disk drive, optical disk drive, magnetic storage device, or the like may be externally connectable to the ultrasound diagnostic device.

Further, the division of function blocks in the block diagrams is merely an example, and a plurality of function blocks may be implemented as one function block, one function block may be divided into a plurality, and a portion of a function may be transferred to another function block. Further, a single hardware or software element may process the functions of a plurality of function blocks having similar functions in parallel or by time division.

Further, the order in which steps described above are executed is for illustrative purposes, and the steps may be in an order other than described above. Further, a portion of the steps described above may be executed simultaneously (in parallel) with another step.

Further, the ultrasound diagnostic device is described as having an externally connected probe and display, but may be configured with an integrated probe and/or display.

Further, according to at least one embodiment, the probe has a structure in which a plurality of piezoelectric elements are arranged in a one-dimensional array. However, probe structure is not limited to this, and may, for example, have a two-dimensional array of transducers in which a plurality of piezoelectric transducers are arranged along two dimensions, or a plurality of transducers in a one-dimensional array may be mechanically swung to acquire a three-dimensional tomographic image, and an appropriate probe may be used depending on a required measurement. For example, when a probe with a two-dimensional array is used, an irradiation position and direction of an ultrasound beam to be transmitted can be controlled by individual changes to timing and voltage applied to the piezoelectric transducers.

Further, a portion of functions of transmitters and receivers may be included in the probe. For example, a transmission electrical signal may be generated and converted to ultrasound in the probe, based on a control signal for generating a transmission electrical signal outputted from the transmitter. It is possible to use a structure that converts received reflected ultrasound into a reception electrical signal and generates a reception signal based on the reception electrical signal in the probe.

Further, at least a portion of functions of each ultrasound diagnostic device pertaining to an embodiment, and each modification thereof, may be combined. Further, the numbers used above are all illustrative, for the purpose of explaining the present invention in detail, and the present disclosure is not limited to the example numbers used above.

Further, the present disclosure includes various modifications that are within the scope of conceivable ideas by a person skilled in the art.

Review (1) The ultrasound diagnostic device according to at least one embodiment of the present disclosure generates images by transmitting and receiving ultrasound to and from a subject via a probe, the ultrasound diagnostic device comprising: ultrasound signal processing circuitry, the ultrasound signal processing circuitry comprising: a transmitter, a receiver, a first image processor, a second image processor, and an image synthesizer. The transmitter alternates between first transmission events that each include transmission of first detection waves and second transmission events that each include transmission of second detection waves. The receiver receives signals based on reflected ultrasound and generates reception signals from the signals. The first image processor repeatedly performs an operation of generating a frame of first images based on reception signals corresponding to a plurality of the first transmission events. The second image processor repeatedly performs an operation of generating a frame of second images based on reception signals corresponding to the second transmission events. The image synthesizer superimposes the second images on the first images to generate and output synthesized images. Frame rate of the second images is higher than frame rate of the first images. The transmitter performs a third transmission event prior to the second transmission events, the third transmission event including transmission of a plurality of the first detection waves to acquire reception signals corresponding to one frame of the first images. The first image processor generates one frame of the first images based on the reception signals corresponding to the third transmission event.

The ultrasound signal processing method according to at least one embodiment comprises: alternating between performing first transmission events that each include transmission of first detection waves and second transmission events that each include transmission of second detection waves; receiving signals based on reflected ultrasound and generating reception signals from the signals; repeatedly performing an operation of generating a frame of first images based on reception signals corresponding to a plurality of the first transmission events; repeatedly performing an operation of generating a frame of second images based on reception signals corresponding to the second transmission events; and superimposing the second images on the first images to generate and output synthesized images. Frame rate of the second images is higher than frame rate of the first images. A third transmission event is performed prior to the second transmission events, the third transmission event including transmission of a plurality of the first detection waves to acquire reception signals corresponding to one frame of the first images. One frame of the first images is generated based on the reception signals corresponding to the third transmission event.

According to the ultrasound diagnostic device or ultrasound signal processing method pertaining to aspects of the present disclosure, even when the frame rate of the second images is improved and frame rate of the first images is low, the first images can be drawn quickly. Accordingly, regardless of a ratio of frame rate of the first images to frame rate of the second images, output images in which the second images are superimposed on the first images can be quickly output, and responsiveness can be improved.

(2) Further, according to at least one embodiment, in transmission of a plurality of the first detection waves to acquire reception signals corresponding to a frame of the first images, propagation directions of the plurality of the first detection waves in the subject are different from each other.

According to this configuration, the first images can be formed by a spatial compound, and a decrease in first image quality can be prevented until completion of a plurality of first transmission events for one frame.

(3) Further, according to at least one embodiment, each of the first transmission events consists of M transmissions of the first detection waves, where M is a natural number, and each of the second transmission events consists of N transmissions of the second detection waves, where N is a natural number.

According to this configuration, frame rates and frame repeat times of the first images and the second images can easily be made uniform.

(4) Further, according to at least one embodiment, one frame of the second images corresponds to one of the second transmission events.

According to this configuration, frame rate of the second images is improved and frame repeat time can be reduced.

(5) Further, according to at least one embodiment, N is determined so that a time required for one of the second transmission events is equal to or less than a defined time.

According to this configuration, frame rate of the second images can be improved in a range that does not decrease frame rate of the first images too much.

(6) Further, according to at least one embodiment, M is determined so that M divided by N is equal to or less than a first defined ratio.

According to this configuration, frame rate of the second images can be sufficiently increased without excessive increase of frame rate of the first images.

(7) Further, according to at least one embodiment, M is determined so that M divided by N is equal to or greater than a second defined ratio.

According to this configuration, an excessive decrease in frame rate of the first images can be prevented.

(8) Further, according to at least one embodiment, M is determined so that a ratio of time required for one of the first transmission events to time required for one of the second transmission events is equal to or less than a third defined ratio.

According to this configuration, frame rate of the second images can be sufficiently increased without excessive increase of frame rate of the first images.

(9) Further, according to at least one embodiment, M is determined so that a ratio of time required for one of the first transmission events to time required for one of the second transmission events is equal to or greater than a fourth defined ratio.

According to this configuration, an excessive decrease in frame rate of the first images can be prevented.

(10) Further, according to at least one embodiment, M is determined so that a ratio of the frame rate of the first images to the frame rate of the second images is equal to or less than a fifth defined ratio.

According to this configuration, frame rate of the second images can be sufficiently increased without excessive increase of frame rate of the first images.

(11) Further, according to at least one embodiment, M is determined so that a ratio of the frame rate of the first images to the frame rate of the second images is equal to or greater than a sixth defined ratio.

According to this configuration, an excessive decrease in frame rate of the first images can be prevented.

(12) Further, according to at least one embodiment, when the transmitter causes transmission of the last second detection wave for one frame of the second images in one of the second transmission events, the second transmission event ends and one of the first transmission events starts.

According to this configuration, a situation in which frame rate or frame repeat time of the second images become spatially or temporally inconsistent can be prevented.

(13) Further, according to at least one embodiment, for at least one of transmission of the first detection waves and transmission of the second detection waves, a dummy transmission is performed at the beginning of a series of transmissions.

According to this configuration, deteriorated reception signal quality in a first detection wave transmission of the first transmission events or the second transmission events can be prevented.

(14) Further, according to at least one embodiment, for transmission of the second detection waves, the transmitter selects a transducer array used for transmission so that with each transmission, a position of the transducer array is moved by a defined distance in a transducer array direction along which the transducers are lined up, and the receiver moves an area used for generation of the reception signals by a defined distance in the transducer array direction along with the movement of the position of the transducer array.

According to this configuration, transmission and corresponding reception processing for one frame of the second images can be uniformly and simply performed.

(15) Further, according to at least one embodiment, the transmitter causes transmission of a plane wave having a different propagation direction for each transmission of the second detection waves in one of the second transmission events, and the receiver generates the reception signals over an entire region of interest, in correspondence with transmission of the second detection waves.

According to this configuration, transmission and corresponding reception for one frame are performed by transmitting plane waves having different propagation directions for each transmission, and therefore the frame rate of the second images can be increased.

(16) Further, according to at least one embodiment, the image synthesizer updates the synthesized images every time a new frame of the first images is generated.

According to this configuration, display and update of the first images can be performed by a simple method.

(17) Further, according to at least one embodiment, the first image processor outputs a partial frame of one of the first images each time a new frame of the second images is generated, and the image synthesizer updates the synthesized images every time a new frame of the second images is generated.

According to this configuration, frame rate of the first images can be improved virtually, and an acquisition time difference between the first images and the second images can be locally reduced.

(18) Further, according to at least one embodiment, the image synthesizer performs frame interpolation of the first images to update the synthesized images every time a new frame of the second images is generated.

According to this configuration, frame rate of the synthesized images can be improved, and an acquisition time difference between the first images and the second images can be locally reduced.

(19) Further, according to at least one embodiment, the image synthesizer performs the frame interpolation by blending a plurality of the first images.

According to this configuration, frame rate of display images can be increased with respect to frame rate of the first images.

(20) Further, according to at least one embodiment, the image synthesizer performs the frame interpolation by motion compensation based on a plurality of the first images.

According to this configuration, frame rate of display images can be increased with respect to frame rate of the first images.

(21) Further, according to at least one embodiment, the first images are B mode images.

According to this configuration, the present disclosure is applied to a combination of B mode images and the second images that have a high frame rate and are superimposed on the B mode images.

(22) Further, according to at least one embodiment, the second images are color Doppler images based on color flow, or power Doppler images.

According to this configuration, a blood flow component can be displayed with high accuracy and responsiveness.

Supplement

The embodiments described above each indicate preferred specific examples of the present disclosure. Numerical values, shapes, materials, constituent elements, arrangement positions and connections of constituent elements, steps, order of steps, and the like indicated as embodiments are merely examples and are not intended to limit the present disclosure. Further, among constituent elements in the embodiments, elements not described in independent claims representing top level concepts of the present disclosure are described as constituent elements constituting a more beneficial embodiment.

Further, the order in which steps described above are executed is for illustrative purposes, and the steps may be in an order other than described above. Further, a portion of the steps described above may be executed simultaneously (in parallel) with another step.

Further, in order to facilitate understanding, constituent elements in each drawing referenced by description of an embodiment are not necessarily to scale. Further, the present disclosure is not limited by the description of each embodiment, and can be appropriately changed without departing from the scope of the present disclosure.

Although the technology pertaining to the present disclosure has been fully described by way of examples with reference to the accompanying drawings, various changes and modifications will be apparent to those skilled in the art. Therefore, unless such changes and modifications depart from the scope of the present disclosure, they should be construed as being included therein.

What is claimed is:

1. An ultrasound diagnostic device that generates images by transmitting and receiving ultrasound to and from a subject via a probe, the ultrasound diagnostic device comprising:
   ultrasound signal processing circuitry, the ultrasound signal processing circuitry comprising:
   a transmitter that interleaves first transmission events that each include transmission of first detection waves and second transmission events that each include transmission of second detection waves;
   a receiver that receives signals based on reflected ultrasound and generates reception signals from the signals;
   a first image processor that repeatedly performs an operation of generating a frame of first images based on reception signals corresponding to a plurality of the first transmission events, wherein each of the first transmission events consists of M transmissions of the first detection waves, M being a natural number that is less than the number of first transmission events required to complete the frame of first images;
   a second image processor that repeatedly performs an operation of generating a frame of second images based on reception signals corresponding to the second transmission events, wherein each of the second transmission events consists of N transmissions of the second detection waves; and
   an image synthesizer that superimposes the second images on the first images to generate and output synthesized images, wherein
   frame rate of the second images is higher than frame rate of the first images and the first image processor generates partial updates of the first images when new frames of the second images are generated,
   the value N is based on an upper limit of time for each of the second transmission events to prevent seam line artifacts from becoming apparent in the partial updates of the first images and the value of M is determined based on the value N and a required pulse repetition frequency of the second images,
   the transmitter performs a third transmission event prior to interleaving the first transmission events and the second transmission events, the third transmission event including transmission of a plurality of the first detection waves to acquire reception signals corresponding to one frame of the first images, and
   the first image processor generates one frame of the first images based on the reception signals corresponding to the third transmission event.

2. The ultrasound diagnostic device of claim 1, wherein in transmission of a plurality of the first detection waves to acquire reception signals corresponding to the frame of the first images, propagation directions of the plurality of the first detection waves in the subject are different from each other.

3. The ultrasound diagnostic device of claim 1, wherein one frame of the second images corresponds to one of the second transmission events.

4. The ultrasound diagnostic device of claim 1, wherein N is determined so that a time required for one of the second transmission events is equal to or less than a defined time.

5. The ultrasound diagnostic device of claim 1, wherein M is determined so that M divided by N is equal to or less than a first defined ratio.

6. The ultrasound diagnostic device of claim 1, wherein M is determined so that M divided by N is equal to or greater than a defined ratio.

7. The ultrasound diagnostic device of claim 4, wherein M is determined so that a ratio of time required for one of the first transmission events to time required for one of the second transmission events is equal to or less than a defined ratio.

8. The ultrasound diagnostic device of claim 4, wherein M is determined so that a ratio of time required for one of the first transmission events to time required for one of the second transmission events is equal to or greater than a defined ratio.

9. The ultrasound diagnostic device of claim 4, wherein M is determined so that a ratio of the frame rate of the first images to the frame rate of the second images is equal to or less than a defined ratio.

10. The ultrasound diagnostic device of claim 4, wherein M is determined so that a ratio of the frame rate of the first images to the frame rate of the second images is equal to or greater than a defined ratio.

11. The ultrasound diagnostic device of claim 1, wherein when the transmitter causes transmission of the last second detection wave for one frame of the second images in one of the second transmission events, the second transmission event ends and one of the first transmission events starts.

12. The ultrasound diagnostic device of claim 1, wherein for at least one of transmission of the first detection waves and transmission of the second detection waves, a dummy transmission is performed at a beginning of a series of transmissions.

13. The ultrasound diagnostic device of claim 1, wherein for transmission of the second detection waves, the transmitter selects a transducer array used for transmission so that with each transmission, a position of the transducer array is moved by a defined distance in a transducer array direction along which transducers of the transducer array are lined up, and the receiver moves an area used for generation of the reception signals by a defined distance in the transducer array direction along with the movement of the position of the transducer array.

14. The ultrasound diagnostic device of claim 1, wherein the transmitter causes transmission of a plane wave having a different propagation direction for each transmission of the second detection waves in one of the second transmission events, and
the receiver generates the reception signals over an entire region of interest, in correspondence with transmission of the second detection waves.

15. The ultrasound diagnostic device of claim 1, wherein the image synthesizer updates the synthesized images every time a new frame of the first images is generated.

16. The ultrasound diagnostic device of claim 1, wherein the first image processor outputs one of the partial updates of the first images each time a new frame of the second images is generated, and
the image synthesizer updates the synthesized images every time a new frame of the second images is generated with the new frame of the second images and the one of the partial updates of the first images.

17. The ultrasound diagnostic device of claim 1, wherein the image synthesizer performs frame interpolation of the first images to update the synthesized images every time a new frame of the second images is generated.

18. The ultrasound diagnostic device of claim 17, wherein the image synthesizer performs the frame interpolation by blending a plurality of the first images.

19. The ultrasound diagnostic device of claim 17, wherein the image synthesizer performs the frame interpolation by motion compensation based on a plurality of the first images.

20. The ultrasound diagnostic device of claim 1, wherein the first images are B mode images.

21. The ultrasound diagnostic device of claim 1, wherein the second images are color Doppler images based on color flow, or power Doppler images.

22. An ultrasound signal processing method comprising:
interleaving first transmission events that each include transmission of first detection waves and second transmission events that each include transmission of second detection waves;
receiving signals based on reflected ultrasound and generating reception signals from the signals;
repeatedly performing an operation of generating a frame of first images based on reception signals corresponding to a plurality of the first transmission events, wherein each of the first transmission events consists of M transmissions of the first detection waves, M being a natural number that is less than the number of first transmission events required to complete the frame of first images;
repeatedly performing an operation of generating a frame of second images based on reception signals corresponding to the second transmission events, wherein each of the second transmission events consists of N transmissions of the second detection waves; and
superimposing the second images on the first images to generate and output synthesized images, wherein
frame rate of the second images is higher than frame rate of the first images and partial updates of the first images are generated when new frames of the second images are generated, the value N is based on an upper limit of time for each of the second transmission events to prevent seam line artifacts from becoming apparent in the partial updates of the first images and the value M is determined based on the value N and a required pulse repetition frequency of the second images,
a third transmission event is performed prior to the interleaving of the first transmission events and the second transmission events, the third transmission event including transmission of a plurality of the first detection waves to acquire reception signals corresponding to one frame of the first images, and
one frame of the first images is generated based on the reception signals corresponding to the third transmission event.

* * * * *